United States Patent
Kim et al.

(10) Patent No.: US 8,313,773 B2
(45) Date of Patent: Nov. 20, 2012

(54) NEAR-INFRARED RESPONSIVE CARBON NANOSTRUCTURES

(75) Inventors: Jin-Woo Kim, Fayetteville, AR (US); Russell Deaton, Fayetteville, AR (US); Vladimir P. Zharov, Little Rock, AR (US)

(73) Assignee: Board of Trustees of the University of Arkansas, Little Rock, AR (US)

( * ) Notice: Subject to any disclaimer, the term of this patent is extended or adjusted under 35 U.S.C. 154(b) by 61 days.

(21) Appl. No.: 12/664,630

(22) PCT Filed: Jun. 13, 2008

(86) PCT No.: PCT/US2008/007450
§ 371 (c)(1),
(2), (4) Date: Dec. 14, 2009

(87) PCT Pub. No.: WO2008/154043
PCT Pub. Date: Dec. 18, 2008

(65) Prior Publication Data
US 2010/0189650 A1    Jul. 29, 2010

Related U.S. Application Data

(60) Provisional application No. 60/943,897, filed on Jun. 14, 2007.

(51) Int. Cl.
*A61K 9/14* (2006.01)
(52) U.S. Cl. ........................................ 424/489
(58) Field of Classification Search .................. None
See application file for complete search history.

(56) References Cited

U.S. PATENT DOCUMENTS

| | | | |
|---|---|---|---|
| 5,688,486 A | 11/1997 | Watson et al. | |
| 6,214,034 B1 | 4/2001 | Azar | |
| 6,479,533 B1 | 11/2002 | Yarosh | |
| 6,530,944 B2 | 3/2003 | West et al. | |
| 6,685,730 B2 | 2/2004 | West et al. | |
| 6,753,287 B1* | 6/2004 | Weisbeck et al. | 502/107 |
| 7,166,557 B2* | 1/2007 | Baker et al. | 502/330 |
| 7,211,320 B1 | 5/2007 | Cooper et al. | |
| 2003/0073573 A1* | 4/2003 | Baker et al. | 502/180 |
| 2005/0272856 A1* | 12/2005 | Cooper et al. | 524/496 |
| 2006/0018829 A1 | 1/2006 | Smith et al. | |
| 2007/0087400 A1 | 4/2007 | Darzins et al. | |
| 2007/0292699 A1* | 12/2007 | Watson et al. | 428/457 |
| 2008/0045865 A1 | 2/2008 | Kislev | |
| 2008/0095714 A1 | 4/2008 | Castella et al. | |
| 2009/0098550 A1 | 4/2009 | Lu et al. | |
| 2009/0123553 A1 | 5/2009 | Reches et al. | |
| 2009/0156976 A1 | 6/2009 | Korbling et al. | |
| 2009/0213369 A1* | 8/2009 | Lee et al. | 356/301 |

OTHER PUBLICATIONS

West, J. and Halas, N., Engineering nanomaterials for bophotonics applications: improving sensing, imaging, and therapeutics, Annual Review of Biomedical Engineering, 2003, p. 285-289, vol. 5, United States.

(Continued)

*Primary Examiner* — Paul Dickinson
(74) *Attorney, Agent, or Firm* — Richard Blakely Glasgow

(57) ABSTRACT

The present invention provides for compositions comprising carbon nanotubes (CNT) and gold (Au). The present invention further provides methods of manufacture of gold-carbon nanotubes (gCNT). The present invention provides methods of using gCNT for biological application.

4 Claims, 15 Drawing Sheets

OTHER PUBLICATIONS

Zharov, V.P., Kim, J.-W., Curiel, S.T., Everts, M., Self assembling nanoclusters in living systems: application for integrated photothermal nanodiagnostics and nanotherapy, Nanomedicine, 2005, p. 326-345, vol. 1, United States.

Averitt, R.D., Sarkar, D., Halas, N.J., Plasmon resonance shifts of Au-coated Au2S nanoshells: insight into multicomponent nanoparticle growth, Physical Review Letters, 1997, p. 4217-4220, United States.

Zharov, V.P., Galitovsky, V., Viegas, M., Photothermal detection of local thermal effects during selective nanophotothermolysis, Applied Physics Letters, 2003, p. 4897-4899, vol. 83, United States.

Pitsillides, C.M., Joe, E.K., Wei, X., Anderson, R.R., Lin, C.P., Selective cell targeting with light-absorbing microparticles and nanoparticles, Biophysical Journal, 2003, p. 4023-4032, vol. 84, United States.

Zharov, V.P., Letfullin, R.R., Galitovskaya, E.N., Microbubblesoverlapping mode for laser killing of cancer cells with absorbing nanoparticle clusters, Journal of Physics D: Applied Physics, 2005, p. 1-11, vol. 38, United States.

Zharov, V.P., Galitovskaya, E.N., Johnson, C., Kelly, T. Synergistic enhancement of selective nanophotothermolysis with gold nanoclusters: Potential for cancer therapy, Lasers in Surgery and Medicine, 2005, p. 219-226, vol. 37, United States.

Hirsh, L.R., Stafford, R.J., Bankson, J.A., Sershen, S.R., Rivera, B., Price, R.E., Hazle, J.D., Halas, N., Nanoshell-mediated near-infrared thermal therapy of tumors under magnetic resonance guidance, Proceedings of the National Academy of Sciences, p. 13549-13554, vol. 100, United States, 2003.

Kam, N.W.S., O'Connell, M., Wisdom, J.A., Dai, H., Carbon nanotubes as multifunctional biological transporters and near-infrared agents for selective cancel cell destruction, Proceedings of the National Academy of Sciences, 2005, p. 11600-11605, vol. 102, United States.

Oldenburg, S.J., Averitt, R.D., Westcott, S.L., and Halas, N.J., Nanoengineering of optical resonances, Chemical Physics Letters, 1998, p. 243-247, vol. 288, United States.

Hirsch, L.R., Stafford, R.J., Bankson, J.A., Sershen, S.R., Rivera, B., Price, R.E., et al., Nanoshell-mediated near-infrared thermal therapy of tumors under magnetic resonance guidance, Proceedings of the National Academy of Sciences, p. 13549-13554, vol. 100, United States, 2003.

Bruchez, M., Moronne, M., Gin, P., Weiss, S., and Alivisatos, A.P., Semiconductor nanocrystals as fluorescent biological labels, Science, 1998, vol. 281, p. 2013-2016, United States.

Chan, W.C., Maxwell, D.J., Gao, X., Bailey, R.E., Han, M., and Nie, S., Luminescent quantum dots for multiplexed biological detection and imaging, Current Opinion in Biotechnology, 2002, vol. 13, p. 40-46, United States.

Chan, W.C., and Nie, S., Quantum dot bioconjugates for ultrasensitive nonisotopic detection, Science, 1998, vol. 281, p. 2016-2018, United States.

Goldman, E.R., Balighian, E.D., Mattoussi, H., Kuno, M.L., Mauro, J.M., Avidin: a natural bridge for quantum dot-antibody conjugates, Journal of the American Chemical Society, 2002, vol. 124, p. 6378-6382, United States.

Brannon-Peppas, L., Polymers in controlled drug delivery, Medical Plastics and Biomaterials, 1997, p. 34-45, United States.

Antonietti, M., and Forster, S., Vesicles and liposomes: a self-assembly principle beyond lipids, Advanced Materials, 2003, vol. 15, p. 1323-1333, United States.

O'Neal, D.P., Hirsch, L.R., Halas, N.J., Payne, J.D., West, J.L., Photothermal tumor ablation in mice using near infrared-absorbing nanoparticles, Cancer Letters, 2004, p. 171-176, vol. 209, United States.

Jain, R.K., The next frontier of molecular medicine: delivery of therapeutics, Nature Medicine, 1998, p. 655-657, vol. 4, United States.

Pluen, A., Boucher, Y., Ramanujan, S., McKee, T.D., Gohongi, T., Di Tomaso, E., Brown, E.B., Izumi, Y., Campbell, R.B., Berk, D.A., and Jain, R.K., Role of tumor-host interactions in interstitial diffusion of macromolecules: cranial vs. subcutaneous tumors, Proceedings of the National Academy of Science, 2001, p. 4628-4633, vol. 98, United States.

Konig, K., Multiphoton microscopy in life sciences, Journal of Microscopy, 2000, p. 83-104, vol. 200, United States.

O'Connell, M.J., Bachilo, S.M., Huffman, C.B., Moore, V.C., Strano, M.S., Haroz, E.H., Rialon, K.L., Boul, P.J., Noon, W.H., Kittrell, C., et al., Band gap fluorescence from individual single-walled carbon nanotubes, Science, 2002, p. 593-596, vol. 297, United States.

Rojas-Chapana, J.A., Troszcynska, J., Firkowska, I., Morsczeck, C. Giersig, M., Multi-walled carbon nanotubes for plasmid delivery into *Escherichia coli* cells, Lab Chip, 2005, p. 536-539, vol. 5, United States.

Lu, Q., Moore, J.M., Huang, G., Mount, A.S., Rao, A.M., Larcom, L.L., Ke, P.C., RNA Polymer Translocation with Single-Walled Carbon Nanotubes, Nano Letters, 2004, p. 2473-2477, vol. 4, United States.

Henry, C.M., Drug delivery, Chemical & Engineering News, 2002, p. 39-47, vol. 80, United States.

Kim, J.W., Kotagiri, N., Deaton, R., and Tung, S., DNA-Directed Self-Assembly of Microscopic 1-D Carbon Nanotube Wire, Proceedings of the 2nd IEEE International, 2007, p. 1044-1047, United States.

Turkevich, J., Stevenson, P.C., and Hillier, J., A Study of the Nucleation and Growth Processes in the Synthesis of Colloidal Gold, Discussions of the Faraday Society, 1951, p. 55-75, vol. 11, United States.

Kim, J.W., and Tung, S., Hybrid Flagellar Motor/MEMS Based TNT Detection System, Proceedings of the International Society for Optical Engineering, 2006, vol. 6223:62230A, United States.

Rose, J.A., Deaton, R., Franceschetti, D.R., Garzon, M., and Stevens, S.E., A statistical mechanical treatment of error in the annealing biostep of DNA computation, Proceedings of the Genetic and Evolutionary Computation Conference, 1999, p. 1829-1834, vol. 2., United States.

Deaton, R., Garzon, M., Rose, J.A., Franceschetti, D.R., Murphy, R.C., and Stevens Jr., S.E., Reliability and efficiency of a DNA based computation, Physical Review Letters, 1998, p. 417, vol. 80, United States.

Frutos, A.G., Liu, Q., Thiel, A.J., Sanner, A.M.W., Condon, A.E., Smith, L.M., and Corn, R.M., Demonstration of a word design strategy for DNA computing on surfaces, Nucleic Acids Research, 1997, p. 4748, vol. 25, United States.

Ben-Dor, A.R., Karp, B., Schwikowski, B., and Yakhini, Z., Universal DNA tag systems: a combinatorial design scheme, Proceedings of the Fourth International Conference on Computational Molecular Biology, 2000, United States.

Santa Lucia, J. A unified view of polymer dumbell, and oligonucleotide DNA nearest-neighbor thermodynamics, Proceedings of the National Academy of Sciences, 1998, p. 1460, vol. 95, United States.

Kim, J.-W., Kotagiri, N., Kim, J.-H., and Deaton, R., In situ fluorescence microscopy visualization and characterization of nanometer scale carbon nanotubes labeled with 1-pyrenebutanoic acid, succinimidyl ester, Applied Physics Letters, 2003, p. 1305-1307, vol. 82, United States.

Kim, J.-W., Shashkov, E.V., Galanzha, E.L., Kotagiri, N., and Zharov, V.P., Photothermal antimicrobial nanotherapy with self-assembling carbon nanotube clusters, Lasers in Surgery and Medicine, 2007, p. 622-634, vol. 39, United States.

Kim, J.-W., Galanzha, E.I., Shashkov, E.V., Moon, H.-M., Zharov, V.P., Golden carbon nanotubes as multimodal photoacoustic and photothermal high-contrast molecular agents, Nature Nanotechnology, 2009, United States.

Galanzha, E.I., Shashkov, E.V., Kelly, T., Kim, J.-W., Yang, L., Zharov, V.P., In vivo magnetic enrichment and multiplex photoacoustic detection of circulating tumour cells, Nature Nanotechnology, 2009, United States.

Galanzha, E.I., Kim, J.-W., Zharov, V.P., Integrated nanotechnology-based photoacoustic and photothermal flow cytometry platform for in-vivo detection and killing of circulating cancer stem cells, Journal of Biophotonics, 2009, p. 1-11, United States.

Galanzha, E.I., Kokoska, M.S., Shashkov, E.V., Kim, J.-W., Tuchin, V.V., Zharov, V.P., In vivo fiber-based multicolor photoacoustic detection and photothermal purging of metastasis in sentinel lymph nodes targeted by nanoparticles, Journal of Biophotonics, 2009, p. 528-539, vol. 2, United States.

Kim, J.-W., Tung, S., Deaton, R., Interfacing Micro-/Nano-Scale Biological and Abiological Materials for Bio/Abio Hybrid Systems, Electrochemical Society Proceedings, 2005, p. 479-493, vol. 2004-13, United States.

Deaton, R., Kim, J.-W., Chen, Junghuei, Design and test of noncrosshybridizing oligonucleotide building blocks for DNA computers and nanostructures, Applied Physics Letters, 2003, p. 1305-1307, vol. 82, United States.

El-Sayed, Ivan H., Huang, Xiaohua, El-Sayed, Mostafa, Selective laser photo-thermal therapy of epithelial carcinoma using anti-EGFR antibody conjugated gold nanoparticles, Cancer Letters, 2006, p. 129-135, vol. 239, United States.

Borer, Philip N., Dengler, Barbara, Tinoco, Ignacio, Uhlenbeck, Olke, Stability of Ribonucleic acid Double-stranded Helices, Journal of Molecular Biology, 1974, p. 843-853, vol. 86, United States.

Hermanson, Greg T., Bioconjugate Techniques, 1996, p. xxi-xxii, 593-597, Academic Press, United States.

Hayat, M.A., Collodial Gold: Principles, Methods, and Applications, 1989, p. xxi, 3, Academic Press, United States.

Averitt, R.D., Westcott, S.L., and Halas, N.J., Linear optical properties of gold nanoshells, Journal of Optical Society of America, 1999, p. 1824-1832, vol. 16, United States.

Brunner, C.S., Product Genesis Report, Challenges and Opportunities in Emerging Drug Delivery Technologies, 2004, p. 1-5, United States.

\* cited by examiner

 
*FIG. 4A*  *FIG. 4B*

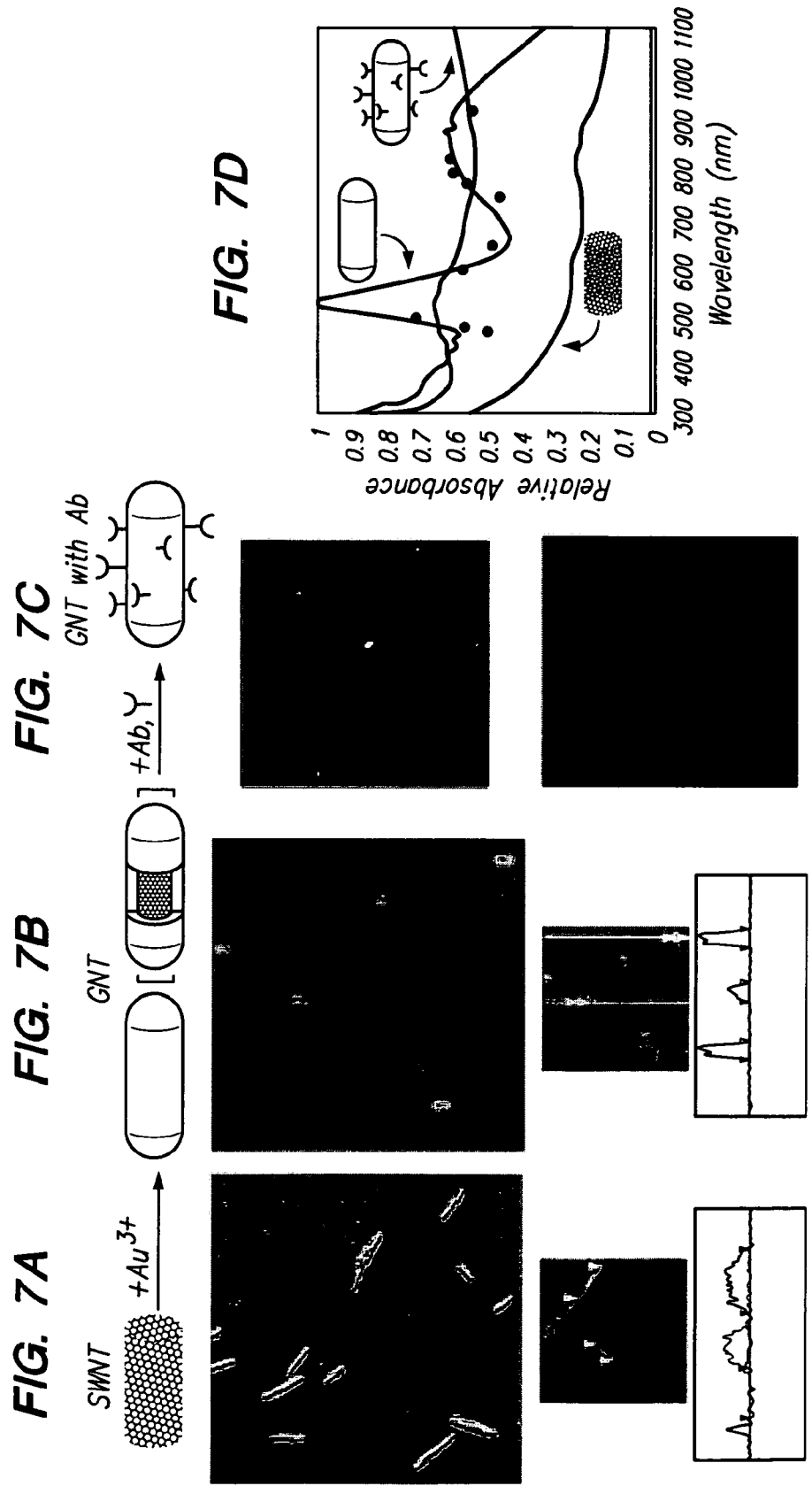

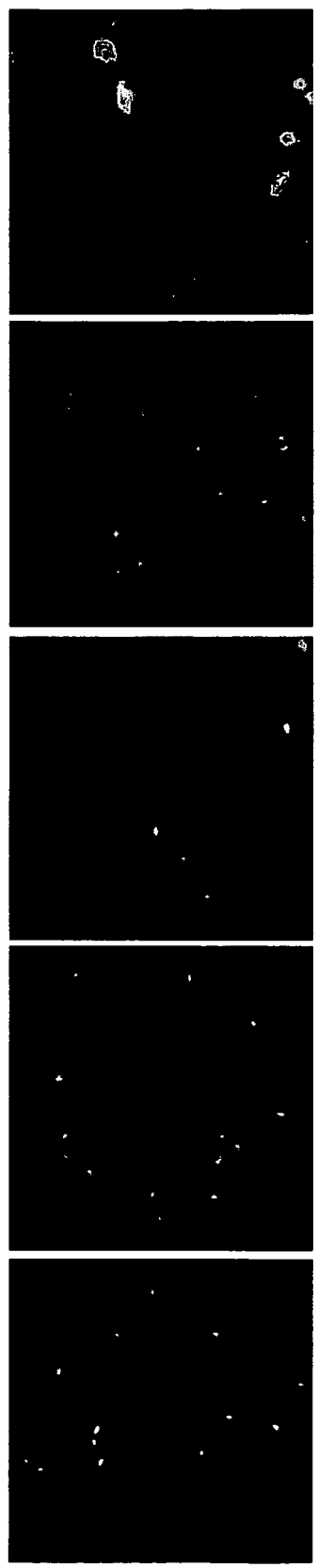

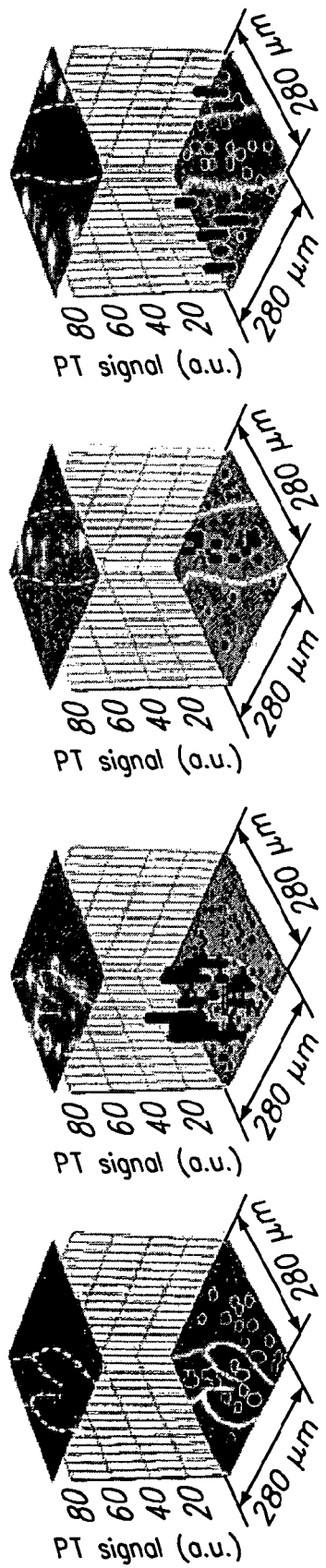
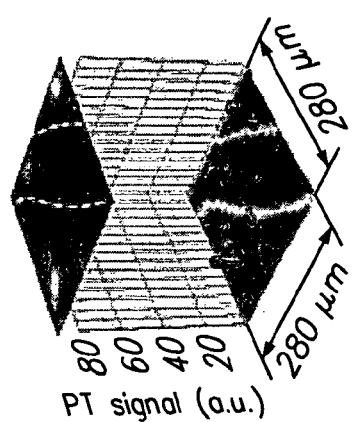
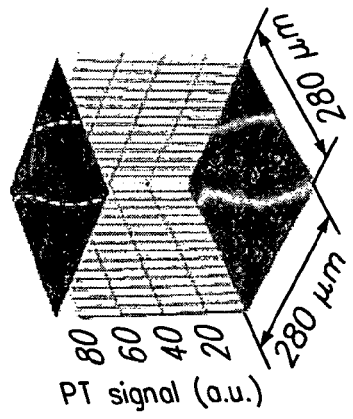
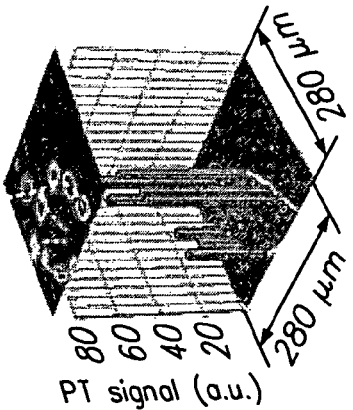
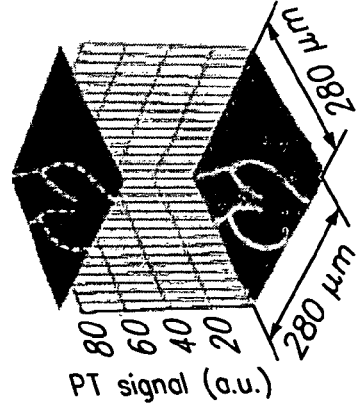

NEAR-INFRARED RESPONSIVE CARBON NANOSTRUCTURES

This application claims priority from the U.S. provisional patent application Ser. No. 60/943,897, entitled "Near-Infrared Responsive Carbon Nanostructures," and filed on Jun. 14, 2007.

FIELD OF THE INVENTION

The present invention provides for compositions and methods for the imaging and treatment of pathologies. Specifically, the present invention provides near-infrared responsive carbon nanostructures. More specifically, the present invention discloses carbon nanotubes (CNTs) layered with gold (Au).

BACKGROUND OF THE INVENTION

A recent report from the National Center for Health Statistics showed that for the first time in over 70 years there was a decline in the actual number of cancer deaths in the United States. Although it is uncertain whether the decline in the total number of cancer deaths will continue, the decline marks an important landmark in the battle against cancer. However, estimates included in the 55$^{th}$ edition of Cancer Facts & Figures project that in 2006, approximately 1.4 million Americans will be diagnosed with cancer and 565,000 will die of the disease. In order to continue to decrease the number of cancer-related deaths, continued development of anti-cancer therapeutics is essential.

Current anti-cancer therapies are generally divided into four major categories: surgery, radiation, chemotherapy, and biologic therapies. Each of these therapies provides certain advantages as well as major drawbacks. For example, although the clinical use of chemotherapeutic agents against cancerous tumors is successful in many cases, they have limited efficacy in many other cases and can cause severe side-effects that limit therapeutic usefulness. These limited efficacies as well as the severe side effects are often the result of a lack of selectivity. Recently, laser-induced thermal and accompanying effects around nanoparticles (NPs) functionalized with specific—bio-ligands have been explored for selective photothermal (PT)-based cancer therapy, suggesting high potentials of PT-based nanotherapeutics for in vivo cancer treatment.

Recent advances in nanotechnology have provided a variety of nanostructured materials with unique and highly controlled properties including exceptionally high strength, the ability to carry conjugates to targets and unique optical properties. By controlling structure at the nanoscale, the properties of nanostructures such as, for example, semiconductor nanocrystals and metal nanoshells can be controlled in a very predictable manner. In addition, the similarity in size of many NPs to biomolecules enables them to be used for applications such as intracellular tagging and makes them ideal candidates for bioconjugate applications such as antibody (Ab) targeting of contrast agents. Thus, these materials can bring new and unique capabilities to a variety of biomedical applications ranging from diagnosis of diseases to novel therapies.

Many of the biomedical and biological applications of nanotechnology involve bioconjugates. The idea of interfacing biological and non-biological systems at the nanoscale level has been investigated for many years. The broad field of bioconjugate chemistry combines the functionalities of biomolecules and abiologically derived molecular species for applications such as markers for research in cellular and molecular biology, biosensing, and biomedical and biological imaging. Major challenges of bioconjugate chemistry include stable and 'controllable' integration and interfacing of the bio- and abio-materials. The stable and 'controllable' interfaces enable us to develop reliable and predictable systems. For example, multiple genes are known to be involved in many diseases, such as, for example, breast and ovarian cancers. However, only a fraction of such genes have been identified and correlated with a particular disease, even after the completion of sequencing of the human genome. In addition, there are more and more observations of alternative splicing, post-translational modifications, and proteolysis of proteins. These discoveries have generated a renewed demand for multiplex bindings of different biocomponents, such as, for example, DNA or Ab, to effectively detect cancerous cells.

Nanostructured materials possess optical properties far superior to the molecular species they replace, such as, for example, higher quantum efficiencies, greater scattering or absorbance cross sections, optical activity over more biocompatible wavelength regimes, and substantially greater chemical stability or stability against photobleaching. Additionally, some nanostructures provide optical properties that are highly dependent on particle size or dimension. The ability to systematically vary the optical properties via structure modification not only improves traditional applications, but also may lead to applications well beyond the scope of conventional molecular bioconjugates.

Quantum dots are nano-sized crystals composed of transition metals such as cadmium, selenium, and technetium, and are highly light absorbing, luminescent NPs whose absorbance onset and emission maximum shift to higher energy with decreasing particle size due to quantum confinement effects. These nanocrystals are typically in the size range of 2-8 nm in diameter. Unlike molecular fluorophores, which typically have very narrow excitation spectra, semiconductor nanocrystals absorb light over a very broad spectral range. This makes it possible to optically excite a broad spectrum of quantum dot "colors" using a single excitation laser wavelength, which may enable one to simultaneously probe several markers in biosensing and assay applications. However, these advantages cannot be realized without first considering the biocompatibility of the materials used. Because the dots are composed of heavy metals, which can be toxic, they have not yet been approved for use in humans. The risk of the heavy metals versus the benefit of obtaining vital information must be weighed.

In many cases, modifications to nanostructures can make them better suited for integration with biological systems; for example, modification of their surface layer may enhance aqueous solubility, biocompatibility, or biorecognition. Nanostructures can also be embedded within other biocompatible materials to provide nanocomposites with unique properties. Surface functionalization with molecular species such as mercaptoacetic acid or the growth of a thin silica layer on a NP's surface may facilitate aqueous solubility. Both the silica layer and the covalent attachment of proteins to the mercaptoacetic acid coating permit the NPs to be at least relatively biocompatible. Quantum dots have also been modified with dihydrolipoic acid to facilitate conjugation of avidin and subsequent binding of biotinylated targeting molecules. Quantum dots can also be embedded within polymer nano- or microparticles to improve biocompatibility while maintaining their unique fluorescence. Specific binding of quantum dots to cell surfaces, cellular uptake, and nuclear localization have all been demonstrated following conjugation of semiconductor nanocrystals to appropriate targeting proteins, such as transferrin or antibodies (Abs).

Embedment of components, such as, for example, bioconjugated NPs, within a carrier has been examined for the potential to avoid physiological barriers. The carrier may be designed to confer solubility and the ability to circulate in the system to avoid accumulation in the liver or spleen. In addition, the carrier may be designed to effectively release the internal components when reaching the target site. Polymer carriers have a greater potential to meet the above requirements over other delivery methods such as liposomes. Because liposomes, spherical vesicles made of ionic lipids, are particles, they are taken up by macrophages. High levels can be found in the liver and spleen, even when the liposomes are coated with polymers. Coated liposomes have other side effects, such as extravasation, in which the liposome moves from the blood vessel into tissue where it may not be wanted. Uncharged hydrophilic polymers, such as polyethylene glycol (PEG) and N-(2-hydroxypropyl) methacrylamide might enable avoidance of accumulation in the liver and spleen. When these polymers are hydrated, they can circulate in the blood for periods of about 1 hour, or 3 hours, or 6 hours, or 12 hours, or 24 hours, or 48 hours or longer. Another advantage of polymers is that the linkage can be designed to control where and when the drug is released. In addition, polymer vesicles have the advantages of superior stability and toughness and offer numerous possibilities for tailoring physical, chemical, and biological properties by variation of block lengths, chemical structure, and conjugation with biomolecules. While liposomes are basically empty vesicles that may be filled with a compound such as a drug, polymers may have a lower drug-carrying capacity. Exemplary use of these vesicles in controlled transmembrane transport and DNA-encapsulation, and controlled release of plasmids for gene transfection have been demonstrated.

Gold colloid has been used in biological and biomedical applications since 1971 when the immunogold staining procedure was invented. The labeling of targeting molecules, such as Abs, with gold NPs has revolutionized the visualization of cellular components. The optical and electron beam contrast properties of gold colloid have provided excellent detection capabilities for applications including immunoblotting, flow cytometry, and hybridization assays. Furthermore, conjugation protocols to attach proteins to gold NPs are robust and simple, and gold NPs have been shown to have excellent biocompatibility.

Gold nanoshells, a new type of gold NPs, are concentric sphere NPs consisting of a dielectric core NP, such as, for example, gold sulfide or silica, surrounded by a thin gold shell. The plasmon-derived optical resonance of gold can be dramatically shifted in wavelength from the visible region into the mid-infrared by varying the relative dimensions of the core and shell layers. Nanoshells may be designed to either strongly absorb (particles less than 75 nm) or scatter the incident light, depending upon their sizes. The gold shell layer is formed using the same chemical methods that are employed to form gold colloid. Thus, the surface properties of gold nanoshells are virtually identical to gold colloid, providing the same ease of bioconjugation and excellent biocompatibility. Intravenous injection of 130 nm gold nanoshells with a maximum absorption near 800 nm followed by continuous-wave laser irradiation has been used to successfully destroy a localized tumor in an animal model.

Gold carbon nanotube (gCNT) rods, are a new type of gold NPs that are concentric rods consisting of a carbon nanotube (CNT) core (either single-walled or multi-walled), surrounded by a thin gold layer. The gCNT is developed by uniquely combining the optical property of CNT and the biocompatibility and bioconjugation potential of gold. Carbon nanotubes are known to have strong absorbance from about 700- to 1,100-nm NIR light, in which biological systems are transparent. Gold is proven to be biocompatible, and is one of a few metals approved by the FDA for human uses. However, gold is not responsive to NIR, limiting its medical application for disease diagnosis and therapy. Therefore, the advantages of both CNT and gold are realized by interfacing gold with CNT. In fact, their interfacing through a chemical reduction process results in an NIR responsive concentric gold nanotube that comprises a CNT core and a layer of gold surrounding the CNT. The similar methods used to form gold colloids are used to form gCNT; thus, gCNT provides excellent biocompatibility and the same simple and robust bioconjugation as gold colloid. Furthermore, GNTs are NIR responsive and the surface plasmon resonance of GNT shows the transverse plasmon absorption at visible region of 520-530 nm as in spherical Au NPs as well as their longitudinal resonance peak in the NIR region near 850 nm as in GNRs. The combination of the CNTs' inherent NIR absorption and the plasmon effects in Au layer around a long CNT tube with very small diameter enable GNTs' synergistic NIR absorption enhancement. Therefore, the NIR responsiveness and biocompatibility of the gCNT allow non-invasive diagnosis and therapy of diseases, such as, for example, cancer.

Furthermore, the ability of CNTs to be spontaneously internalized by cells has recently excited numerous studies on transporting peptides, DNA, and RNA inside cells, both eukaryotic and prokaryotic, for tissue specific gene/drug delivery. The gCNT's smaller diameter, rod-like shape with hollow core, and less rigidity (close to CNT's mechanical properties) could provide better penetration to cells as compared to spherical gold nanoshells, thereby overcoming a limitation in the use of this class of nanostructures in the photothermal therapy of cancer. In addition, gCNTs could provide better targeting to small cell-surface biomolecules (5-10 nm), better clustering capability, and possibility to carry therapeutic payloads in their hollow cores.

BRIEF DESCRIPTION OF THE DRAWINGS

FIG. 4 illustrates TEM images of well-dispersed, shortened (ds) SWNT (A) and MWNT (B). Scale bars represent 500 nm.

FIG. 7 illustrates AFM images(i) as well as AFM section analysis results (ii) of SWNTs (a) and gCNTs (b). Scale bars represent 100 nm (c) Epi-fluorescence images of (i) gCNTs conjugated with ImmunoPure® Rabbit Anti-Chicken IgY Ab (Pierce Biotechnology) and (ii) unconjugated gCNTs after attachment of fluorescein-labeled secondary Ab (ImmunoPure® Fluorescein Conjugated Goat Anti-Rabbit IgG, Pierce Biotechnology). (d) Normalized UV/vis/NIR plasmon-derived optical resonances of: gCNTs in ddH$_2$O (light gray line), Ab-conjugated gCNTs in ddH$_2$O (dark gray line), dsSWNT in ddH$_2$O (black line), and ddH$_2$O only (dots). The UV/vis/NIR optical spectra were normalized on the maximal absorption at the wavelength range of 300 and 1,100 nm of the combined plasmon responses of SWNTs and gCNTs, which were adjusted according to the yield estimations. Normalized PA signal amplitudes of individual GNTs in ddH$_2$O (dots) at different laser wavelengths (8-ns pulse width and laser fluence of 40 mJ/cm$^2$), which were normalized on the maximal PA amplitudes at the wavelength range of 300 and 1,100 nm.

FIG. 9 illustrates EPI-fluorescence images of E. coli with well-dispersed SWNT on cell membrane or in the cell after multi-laser exposures of 50 pulses, wavelength of 1064 nm and pulse duration of 12 ns at various laser energies: (a) No laser exposure, (b) 0.3 J/cm$^2$, (c) 1 J/cm$^2$, (d) 2 J/cm$^2$, and (e) 3 J/cm$^2$. Samples before and after laser exposures were stained and evaluated after staining them with LIVE/DEAD® BacLight™ Bacterial Viability Kit (Invitrogen, Carlsbad, Calif.). Live cells were green and dead cells red with EPI-fluorescence imaging. Arrows in (e) indicate lysed cells after laser exposure.

DETAILED DESCRIPTION OF THE PREFERRED EMBODIMENT

Figure 1:
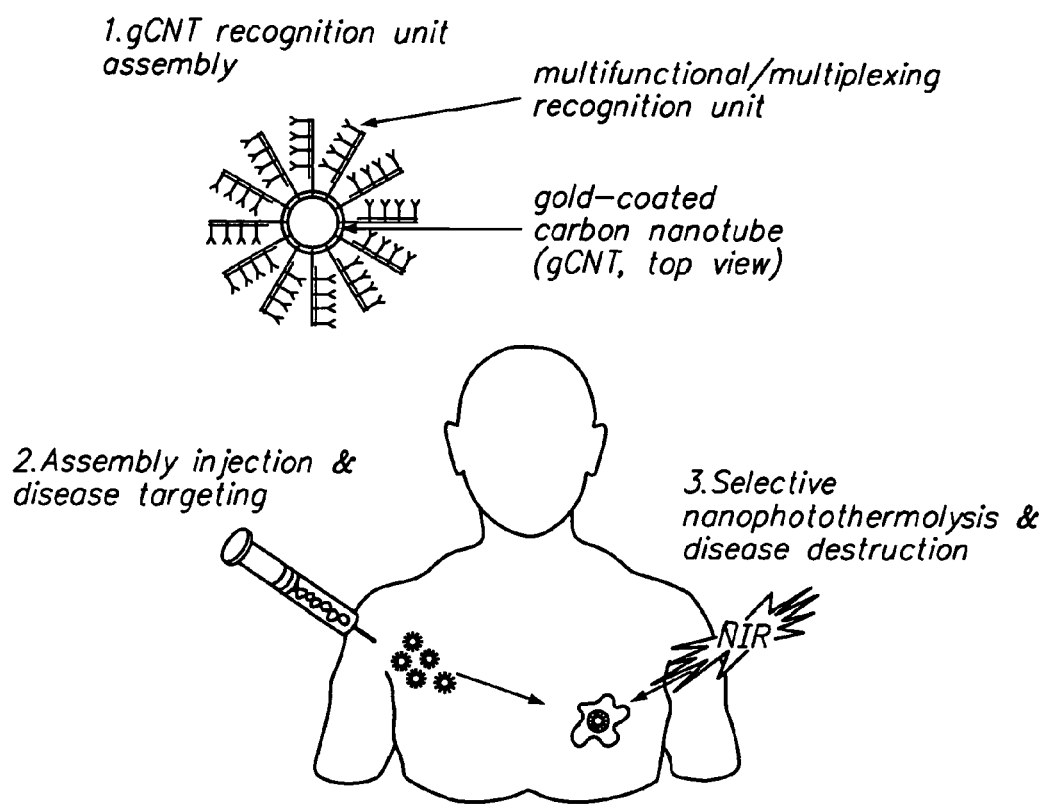
FIG. 1 illustrates an overview of a method of GNT based photothermolysis.

The present invention is more particularly described in the following description and examples that are intended as being illustrative and not limiting as various modifications or substitutions will be apparent to those skilled in the art.

The term gold refers to elemental gold (Au) or salts thereof.

The term carbon nanostructure refers to a molecular structure comprising a plurality of carbon atoms. A carbon nanostructure may be, for example, either a single-walled carbon nanotube (SWNT) or a multi-walled carbon nanotube (MWNT). A carbon nanostructure may be, for example, a fullerene.

The term carbon nanotube refers to a molecular structure comprising a plurality of carbon atoms, having a first end, an opposite, second end, and a body portion defined there between. Each carbon atom at the first and second end is chemically coupled with a corresponding hydrogen atom. The body portion is formed with a carbon wall and has an interior surface defining a cavity, an opposite, exterior surface and a longitudinal axis there through the cavity.

The term single walled carbon-nanotube (SWNT) refers to a carbon nanotube wherein the body portion is a single carbon wall.

The term multi-walled carbon nanotube (MWNT) refers to a carbon nanotube wherein the body portion comprises a plurality of carbon walls.

The term targeting moiety refers to any first moiety that specifically binds to a second moiety. A targeting moiety may be, for example, an antibody, wherein said antibody binds an antigen, said antigen being the aforementioned second moiety. Nothing precludes the possibility that an antibody could also be the target of some other targeting molecule, such as, for example, an Fc receptor which may bind the constant region of some antibody molecules. A targeting moiety may be selected from the group consisting of Abs, deoxyribonucleic acids, peptide nucleic acids, proteins, protein fragments, and small molecules.

Additionally, the gold carbon nanotubes posses the ability to carry therapeutic agents or chemicals, such as magnetic materials, Abs, deoxyribonucleic acids, peptide nucleic acids, proteins, protein fragments, and small molecules either as attachments to the outside and/or within their empty core space. The term antibody refers to an intact antibody, or a binding fragment thereof that competes with the intact antibody for epitope binding. Binding fragments may be produced by recombinant DNA techniques, or by enzymatic or chemical cleavage of intact Abs. Binding fragments include Fab, Fab', F(ab')$_2$, Fv, and single-chain Abs. Furthermore, antibody includes humanized Abs as well as human Abs and Abs of other species.

The term near-infrared responsive refers to the absorbance of near-infrared radiation by a molecule.

The term photothermolysis refers to the lysis of cells or structural degradation of non-cellular entities through administration of near-infrared radiation to a near-infrared responsive composition of matter located in proximity to said cells or noncellular entities.

The term nanophotothermolysis refers to photothermolysis wherein the near-infrared responsive composition of matter comprises a carbon nanostructure and gold (Au).

The term disease refers to any pathology, including, but not limited to, malignant hyperplasia, benign hyperplasia, heart disease, atherosclerosis, Alzheimer's, bacterial infection, fungal infection, viral infection and parasitic infection.

The term contrast agent refers to a compound administered to a mammal for imaging anatomical structures.

The functionalization strategy of the present invention provides for, when desired, a significant level of control over the locations, orientations, and compositions of the functional ligand groups. Furthermore, the functionalization strategies increase the water solubility of the NPs: As examples, both the number of functional groups per particle and the orientations of the functional groups are controllable. These factors also allow for selective bioconjugation with multiple ligands, enabling multi-functional and multi-plexing utility.

In one embodiment of the present invention, a near-infrared responsive composition of matter comprising a carbon nanostructure and gold (Au) is disclosed. The carbon nanostructure comprises a plurality of carbon atoms. A carbon nanostructure may be, for example, either a single-walled carbon nanotube (SWNT) or a multi-walled carbon nanotube (MWNT). A SWNT may be, for example, a molecular structure comprising a plurality of carbon atoms, having a first end, an opposite, second end, and a body portion defined there between. Each carbon atom at the first and second end is chemically coupled with a corresponding hydrogen atom. The body portion is formed with a carbon wall and has an interior surface defining a cavity, an opposite, exterior surface and a longitudinal axis there through the cavity.

In one embodiment of the present invention, a therapeutic agent comprising a near-infrared responsive composition of matter comprising a carbon nanostructure and gold (Au) is disclosed. Said carbon nanostructure may be, for example, a fullerene.

In another embodiment of the present invention, a therapeutic agent comprising a near-infrared responsive composition of matter comprising a carbon nanostructure and gold (Au) is disclosed. Said carbon nanostructure may be, for example, a multi-walled carbon nanotube.

In one embodiment of the present invention, the therapeutic agent comprising a near-infrared responsive composition of matter comprising a carbon nanostructure and gold (Au) may further comprise a targeting moiety. Said targeting moiety may be, for example, an antibody.

In one aspect of the present invention, a diagnostic contrast agent comprising a near-infrared responsive composition of matter comprising a carbon nanostructure and gold (Au) is disclosed. Said carbon nanostructure may be, for example, a single-walled carbon nanotube. Said carbon nanostructure may be, for example, a multi-walled carbon nanotube.

In one embodiment of the present invention, the diagnostic contrast agent comprising a near-infrared responsive composition of matter comprising a carbon nanostructure and gold (Au) may further comprise a targeting moiety. Said targeting moiety may be, for example, an antibody.

In one embodiment of the present invention, a method of manufacture of a near-infrared responsive composition of matter comprising a carbon nanostructure and gold (Au) is disclosed. The method of manufacture may comprise, for example, the following:
(a) obtaining carbon nanostructures;
(b) obtaining gold;
(c) obtaining reagents;
(d) combining the reagents, gold and carbon nanostructures; and
(e) isolating the near-infrared responsive composition of matter comprising a carbon nanostructure and gold (Au).

In one aspect of the present invention, a method of diagnosis of a disease in a mammal is disclosed. The method of diagnosis of a disease may comprise, for example, the following:
(a) administering to a mammal a diagnostic contrast agent comprising a carbon
nanostructure and gold (Au); and
(b) visualizing the diagnostic contrast agent.

The method of diagnosis of a disease may be implemented to diagnose many diseases. The disease to be diagnosed may be, for example, selected from the group consisting of malignant hyperplasia, benign hyperplasia, bacterial infection, fungal infection, viral infection and parasitic infection.

In one aspect of the present invention, a method of photothermolysis is disclosed. The method of photothermolysis may comprise, for example, the following:
(a) administering to a mammal a near-infrared responsive composition of
matter comprising a carbon nanostructure and gold (Au); and
(b) administering near-infrared radiation to said mammal.

In one aspect of the present invention, a kit comprising a carbon nanostructure and gold (Au) is disclosed. The kit may further comprise a targeting moiety. Said targeting moiety may be, for example, an antibody.

Figure 2:
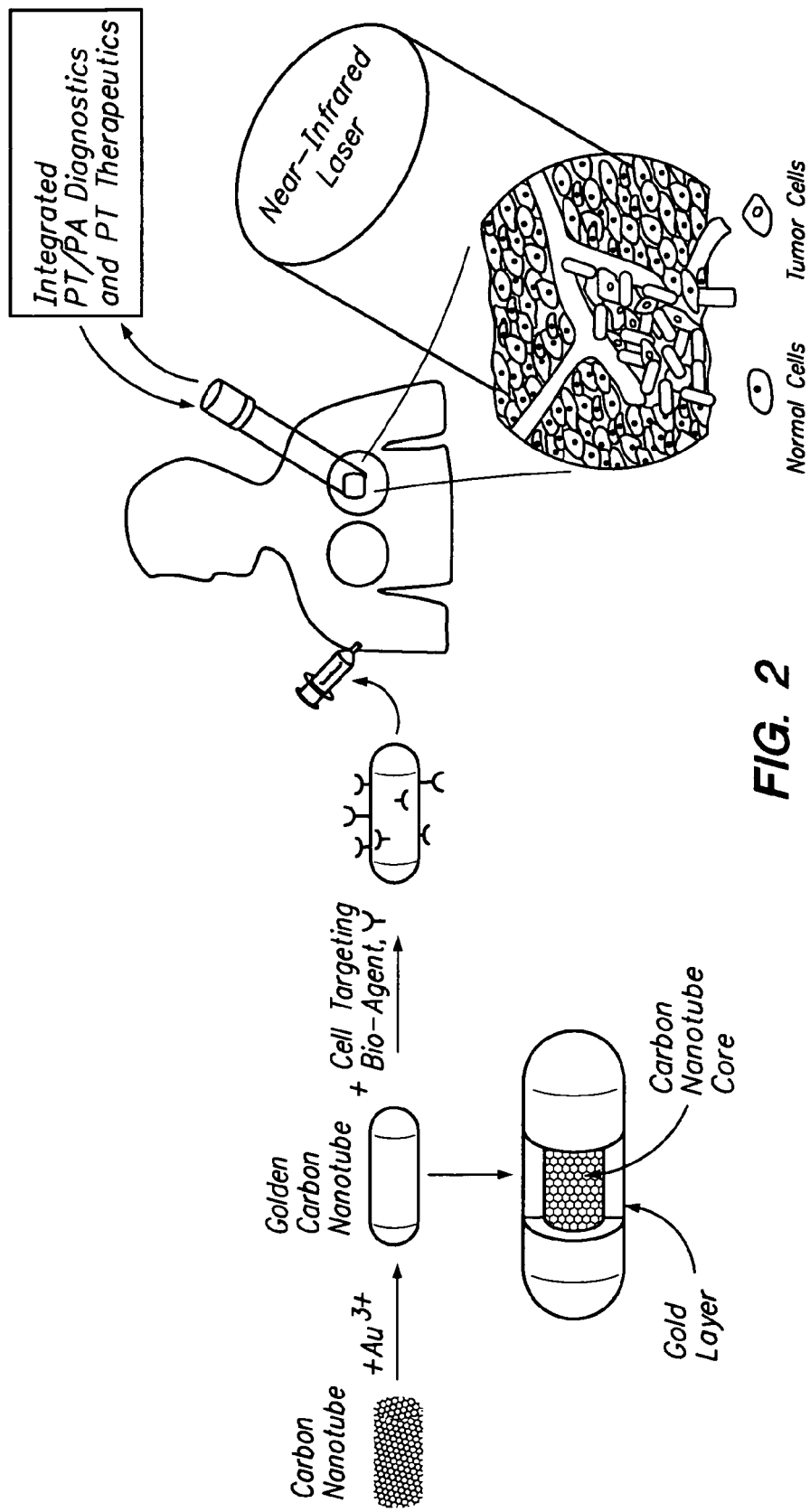
FIG. 2 illustrates schematic of the integrated photothermal (PT) and photoacoustic (PA) nanodiagnostics and nanotherapeutics with gCNT contrast agent in vivo.

In one aspect of the present invention, a gold-coated carbon nanotube (gCNT) rod system for non-invasive cancer therapy with gCNT as a near-infrared (NIR) responsive agent is disclosed. This gCNT may be functionalized with multifunctional and multiplexing recognition units thereby allowing self-assembly for more selective and specific target recognition (FIG. 1 and FIG. 2).

The compositions and methods of the present invention enable NIR responsive, minimally invasive photoacoustic (PA) and photothermal (PT) therapy, and selective and controllable recognition units to maximize target recognition efficacy. Specifically, the present invention discloses NIR responsive concentric gCNT by uniquely pairing the advantages of CNT and gold with, for example, DNA-guided assembly of multifunctional and multiplexing recognition units on the gCNT.

The data show that the unique approach described here is a valuable new weapon against disease, including, but not limited to cancer.

Figure 3:
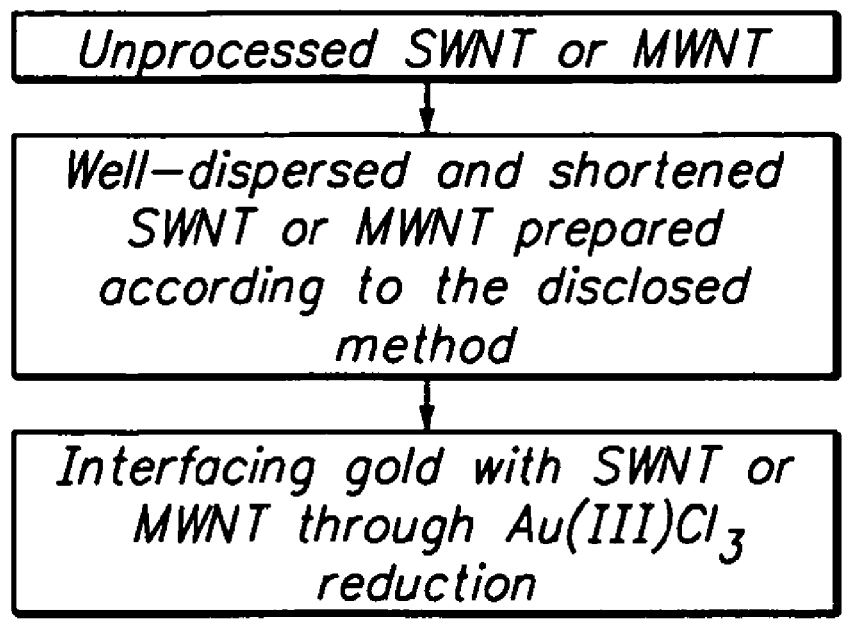
FIG. 3 illustrates the production process of the GNT. The GNT may be assembled using unprocessed SWNT and MWNT in combination with Au(III) $Cl_3$ reduction for creation of the gold interface. CNTs play dual roles as substrates as well as reducing agents. The Au deposition process does not require additional reducing agents such as citrate for colloidal Au preparation or external voltage sources.

FIG. 3 illustrates a schematic of the gCNT production process which results in a composition of matter that has the optical properties of CNT and the biocompatibility and bioconjugation properties of gold. Briefly, well-dispersed and shortened single-walled (SWNT) or multi-walled nanotubes (MWNT) are prepared according to established methods. Such SWNT and MWNT are commercially available, but they may also be prepared on site according to methods common in the art. Au(III)Cl3 reduction is subsequently utilized for interfacing gold with the CNT without the aid of additional reducing agents such as citrate for colloidal Au preparation or external voltage sources (in other words, CNTs play dual roles as substrates as well as reducing agents).

Figures 5A, 5B, 5C, 5D:
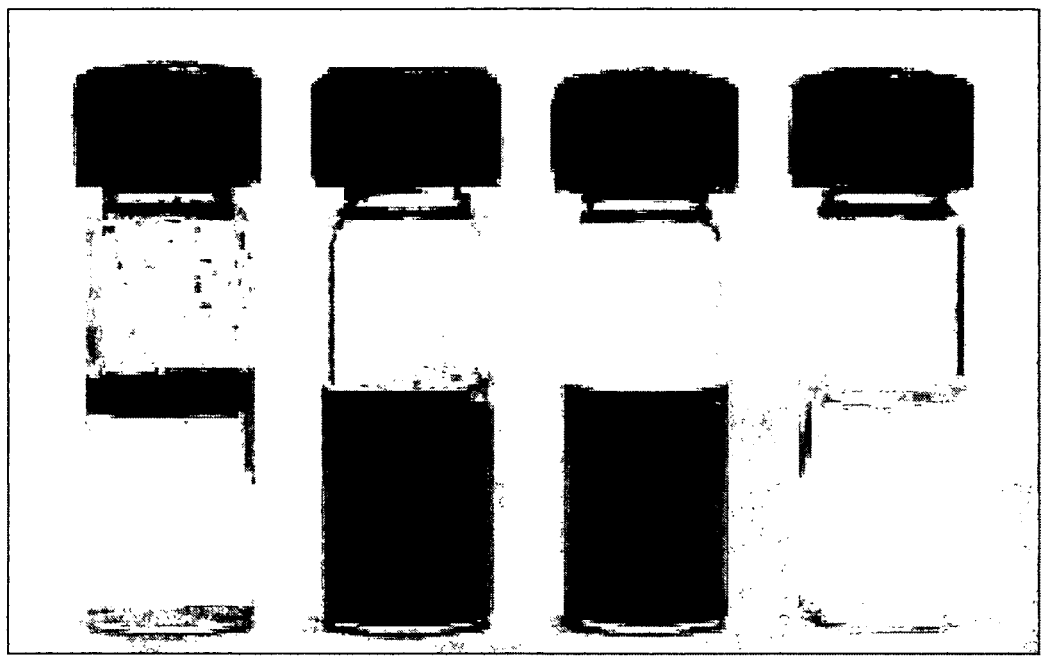
FIG. 5 illustrates a visual comparison of SWNT solutions in distilled water of the starting material (A), the acid-refluxed (B), the acid-refluxed after 30 min (C), and the acid-refluxed and centrifuged after 6 months (D).

SWNT and MWNT were purchased from Carbon Nanotechnologies Inc. (Houston, Tex.) and Nano-lab Inc. (Newton, Mass.). The purchased CNTs were purified by acid refluxing by sonicating in HNO3 (0.1 mg-CNT/mL) for 1 hr (SWNT) or 4 hr (MWNT) followed by H2SO4:HNO3 (3:1) mixture for 12 hr (SWNT) or 24 hr (MWNT). The acid-refluxed samples were filtered using a 100 nm hydrophilic polycarbonate filter (Millipore), followed by washing three times with distilled water supplemented with 0.2% sodium dodecylbenzenesulfonate (NaDBS). The purified CNTs were reconstituted in 1 mL of distilled water. The CNT solutions were further centrifuged at 14,000×g for 40 minutes at 25° C. to remove non-dispersed CNT aggregates, yielding the supernatant with CNTs that are well-dispersed, shortened and oxidized at the tips, as exemplified in TEM images (FIG. 4). From analyses of the TEM images, the average length and diameter of dsSWNT was estimated to be 186 nm with a standard deviation (SD) of 46.7 nm and 1.7 nm with an SD of 0.14 nm, respectively. For dsMWNT, the average length and diameter was 376 nm with an SD of 35.2 nm and 19.0 nm with an SD of 2.92 nm, respectively. The estimated diameters are comparable with those in manufacturer's specification (0.8-1.2 nm for SWNT and 10-30 nm for MWNT). The resultant dsSWNT and dsMWNT suspensions remained stable even after six months (FIG. 5). Polydispersity and poor solubility of CNTs impose a considerable challenge for their practical applications. This method provided very effective and stable dispersion of CNTs in aqueous solutions.

Figure 6:
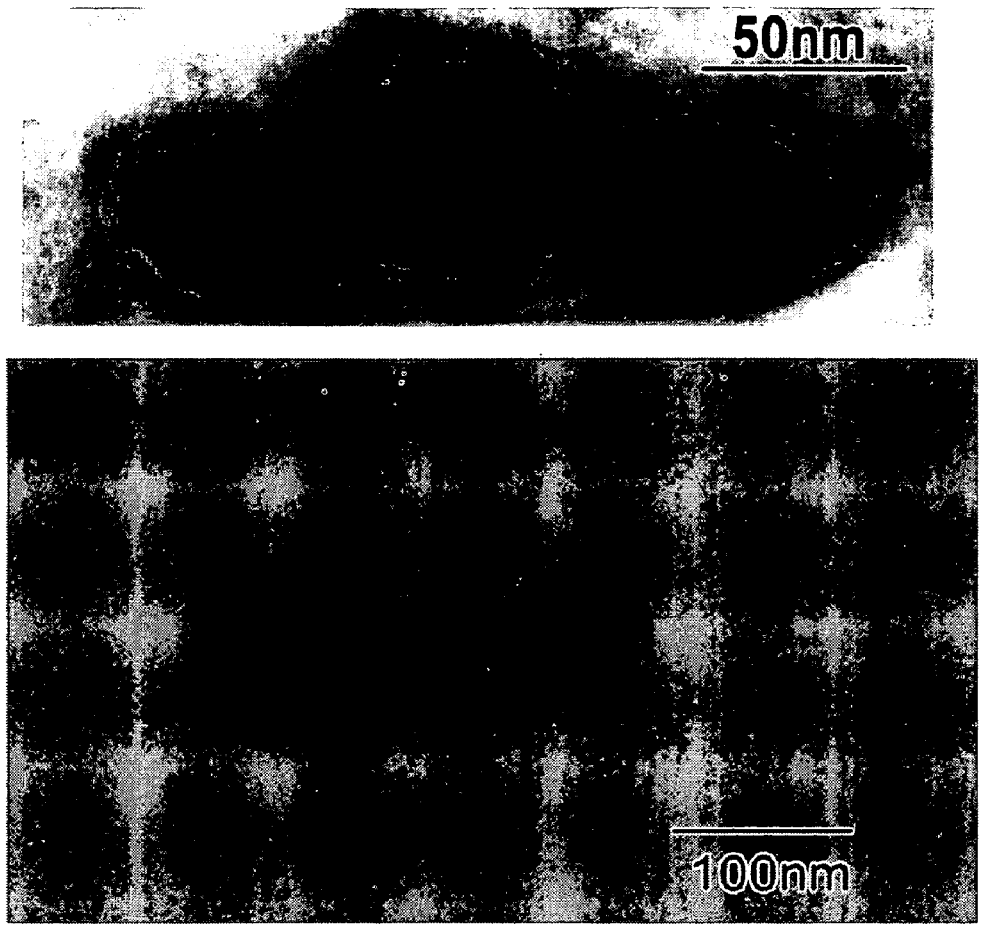
FIG. 6 illustrates TEM images of gCNTs with SWNT (top panel) and gCNTs with MWNT (bottom panel).

The gCNT was prepared by interfacing gold (Au) with the dsSWNT and dsMWNT through Au(III)Cl3 reduction. Various thicknesses of gold layers were coated by controlling the time of Au(III)Cl3 reduction as well as the initial Au(III)Cl3 concentration. SWNTs play dual roles as substrates as well as reducing agents. The reaction medium for the Au deposition consisted of 5 wet-% dsSWNT or dsMWNT solution and 95 wet-% of aqueous solution containing various concentrations of $HAuCl_4$. The reaction mixture was incubated at room temperature (23° C.) with a gentle mixing. The reaction proceeded over various periods. The resultant gCNTs were harvested and washed three times with distilled water after centrifugation at 10,000×g for 5 min to remove the remaining reactants i.e., $HAuCl_4$ and SWNTs. The resultant gCNTs were reconstituted in the water. Their sizes were estimated using AFM and TEM, and their optical properties were evaluated using UV-vis spectrophotometer. FIG. 6 illustrates TEM images of gSWNT (top) and gMWNT (bottom) synthesized in the reaction conditions of 5 mM HAuCl4 and 5 min incubation. FIG. 7 illustrates AFM images of dSWNT (a) and gSWNT (b) produced under the same conditions. The surface characteristics of dsSWNTs (FIG. 7 a) and gSWNTs (FIG. 7 b) are clearly different. The gSWNT surfaces are smoother and have distinctive 'bumps', indicating more than one Au nucleation and their growth on SWNT surfaces. FIG. 7b ii shows rod-like shapes of gCNTs with two or three slight Au bumps with minimal gaps between them, indicating not only multiple nucleations and their growths on SWNT but also the complete coverage of gold on the SWNT surface.

FIG. 7d illustrates the normalized plasmon-derived optical resonance of gCNTs, showing their transverse plasmon absorption at visible region of 520-530 nm as in spherical Au NPs as well as their longitudinal resonance peak in the MR region near 850 nm as in gold nanorods (GNRs) (red line). The conventional spectral data for many GNTs in suspension were in good agreement with the PA spectra obtained from a single GNT (symbols), demonstrating gCNTs' potential as NIR high contrast PA agents. The gCNTs' plasmon responses in visible as well as NIR were significantly higher than those for the shortened SWNTs (gray line). The PA signals from rare gCNT clusters with the average size of 250-300 nm were 10-15 times stronger in amplitude compared to that from the individual gCNTs in analogy to CNT clusters. FIG. 7 c illustrates the epi-fluorescence microscopy after attachment of fluorescein-labeled secondary Abs, confirming the gCNTs' capability for simple and robust bioconjugation. After Ab conjugation, gCNT absorption peak of the transverse plasmon resonance decreased substantially, while the longitudinal plasmon resonance peak was slightly red-shifted to ~1,000 nm without notable change in its intensity (green line in FIG. 7 d). This is related to the changes in the surface characteristics as well as the local refractive index by Abs on the particles.

Well-defined and stable interfaces between NPs and biocomponents are useful for developing and implementing a DNA-guided assembly of multifunctional/multiplexing recognition units on the gCNT. Specific and selective molecular recognition properties of chemical moieties, proteins, and DNA are a foundation of the self-assembly process. The gCNT can be easily conjugated with biological/biochemical targeting molecules, such as Abs and DNA, by the same protocols developed for gold colloids.

Antibodies and DNA oligonucleotides were coupled to gold NPs by the alkane thiol method. To thiolize gCNTs, the retentates after filtration at the final stage of gCNT production were reconstituted in 1 mL of 50% ethanol solution. Mercaptohexanol was added to the gCNT solution at a final concentration of 1 mM, and the mixture was incubated 5 minutes at 25° C. After incubation, the remaining mercaptohexanol in the reaction medium was removed by filtration using 100 nm hydrophilic polycarbonate filter (Millipore) and washing three times using the potassium phosphate buffer (5 mM, pH 7.0) supplemented with 50 mM NaCl. For Abs, thiol groups are generated by treating the Abs with dithiothreitol (DTT) to reduce disulfide bonds. Designed oligonucleotides with 5'-thiol modifications were purchased from commercial vendors, such as IDT-DNA (Coralville, Iowa). To functionalize gCNTs and biocomponents, the reduced Abs (10 µl) or 5'-modified DNAs (1 µl) were added to the thiolized gCNT solution in the phosphate buffer to the final concentration of 10 wet-%. The reaction mixtures were incubated for 2 hr at 25° C. and the reaction was terminated through the aforementioned filtration and washing step. The resultant bio/abio hybrids were examined using TEM. FIG. 8G illustrates DNA-guided clustering of gSWNT through hybridization of complementary DNA sequences attached to the sidewalls of gSWNT according to the aforementioned method.

Figure 8A:
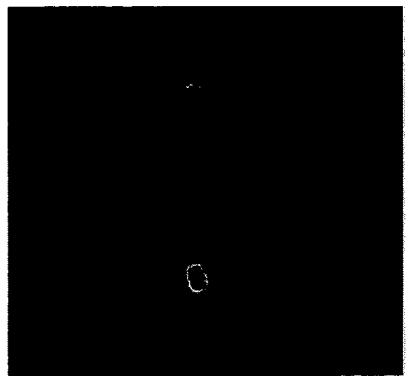
FIG. 8 illustrates examples of bio/abio hybrids through controlled and stable interfacing. (A) An Epi-fluorescent image of DNA (green dots) immobilized by alkane thiol. (B) Light-microscopy image of E. coli with polystyrene (d=200 nm) attached through Abs directed against the K-type stain of E. coli. (C) TEM image of the DNAs functionalized to tips of CNT. (D) TEM image of 1-D self assembly of DNA-CNT conjugates. (E) AFM image of the diamine-coupled Au dimmers of mono-functionalized Au nanoparticles (Circles indicates Au dimmers, scale bar, 140 nm). (F) AFM image of the diamine-coupled 1-D Au chain of bifunctionalized Au nanoparticles (Circles indicates the 1-D Au chain, scale bar, 60 nm). (G) TEM image of DNA-guided clustering of Au-coated CNT.

Thiolated oligonucleotides may be coupled to gold NPs by the alkane thiol method (FIG. 8A).

Figure 8B:
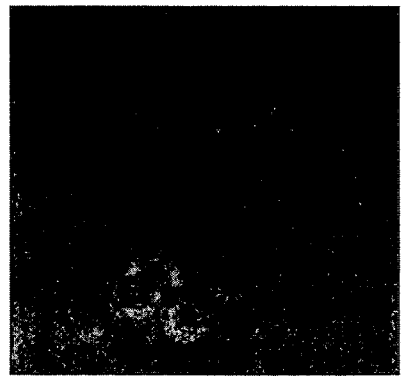

Polystyrene beads may be attached to 200 nm Au as well as to E. coli cells through antibody conjugation (FIG. 8B), for the development of flagellar motor based hybrid systems. In this particular example, Abs were attached to the surface of the beads through biotin-streptavidin conjugation.

Figure 8C:
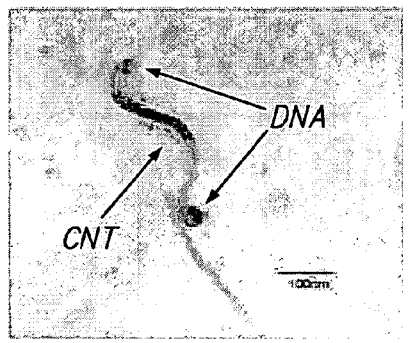
Figure 8D:
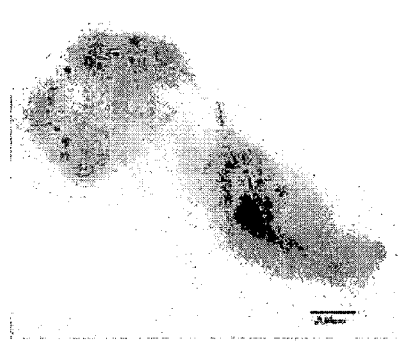
Figure 8E:
Figure 8F:
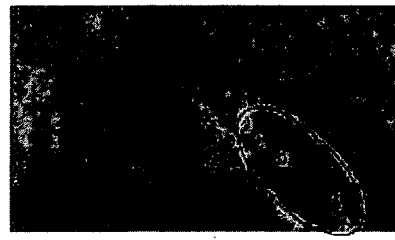
Figure 8G:
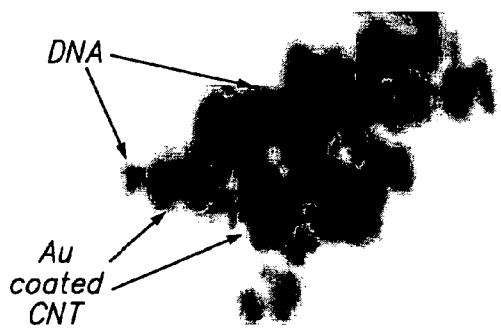

In addition, DNA was attached to the tips of carbon nanotubes (CNTs) (FIG. 8C) with the goal of self-assembling complicated nanostructures with greater control of component location. A one-dimensional self-assembly of DNA-CNT conjugates was achieved through the controlled interfacing of CNT and DNA (FIG. 8D). Furthermore, a mono-functionalized, i.e. one carboxyl group, as well as bi-functionalized, i.e. two carboxyl groups, gold nanoparticles were synthesized through the solid-phase place exchange reaction and the modified nanoparticles were coupled through the diamine coupling reaction to form dimmers (FIG. 8E) and 1-D gold chain (FIG. 8F). The results demonstrate well-defined and stable interfaces between CNT, gold, DNA and other biological components.

Figure 10A:
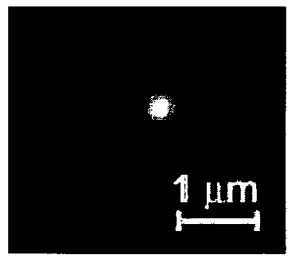
FIG. 10 represents PT images (a-c), PT responses (d-f), and PA signals (g-i) from gSWNTs under single laser pulse (8-ns pulse with and wavelength of 850 nm). The laser fluence and time delay were (a) 10 mJ/cm$^2$ and 5 ns, (b) 55 mJ/cm$^2$ and 5 ns, and (c) 0.2 J/cm$^2$ and 70 ns. Amplitude (vertical axis), time scale (horizontal axis), and laser fluence were (d) 25 mV, 1 µs/div, and 20 mJ/cm$^2$, (e) 200 mV, 1 µs/div, and 60 mJ/cm$^2$, (f) 500 mV, 2 µs/div, and 0.2 J/cm$^2$, (g) 50 mV, 2 µs/div, and 15 mJ/cm$^2$, (h) 100 mV, 1 µs/div, and 55 mJ/cm$^2$, and (i) 500 mV, 2 µs/div, and 0.2 J/cm$^2$. (j) PA signal amplitudes from gCNTs as function of laser fluence. (k) PA signals from gCNTs as function of laser pulse number at various laser fluences: 7.30 J/cm$^2$ (filled circle), 1.87 J/cm$^2$ (filled square), 0.29 J/cm$^2$ (filled triangle), 0.03 J/cm$^2$ (filled diamond), and 0.01 J/cm$^2$ (open circle). Laser wavelength was 850 nm.
Figure 10B:
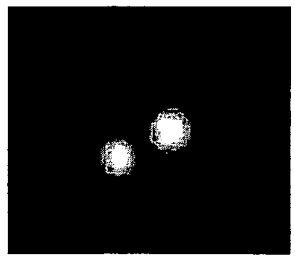
Figure 10C:
Figure 10D:
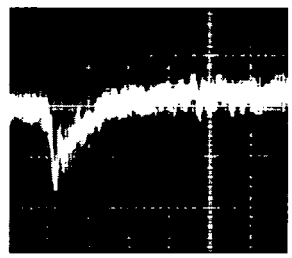
Figure 10E:
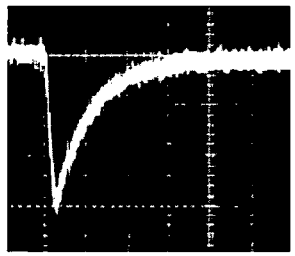
Figure 10F:
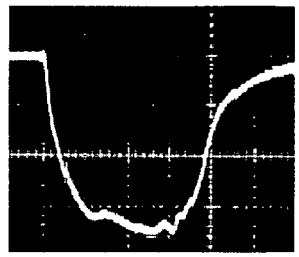
Figure 10G:
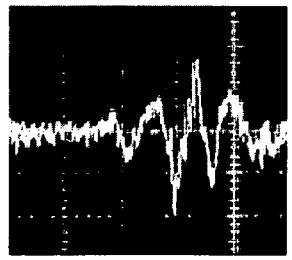
Figure 10H:
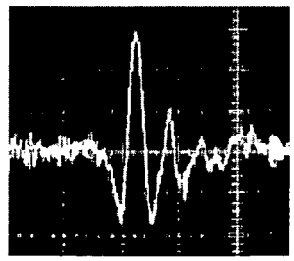
Figure 10I:
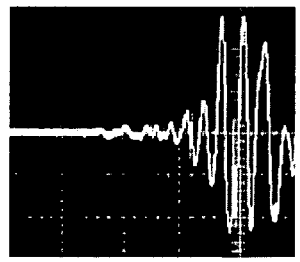
Figure 10J:
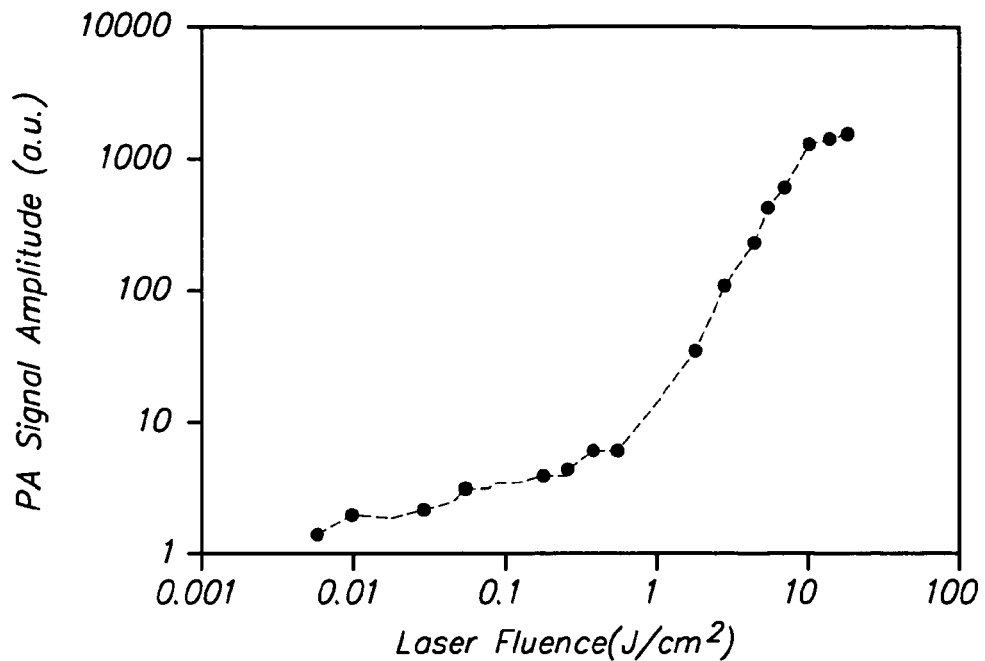
Figure 10K:
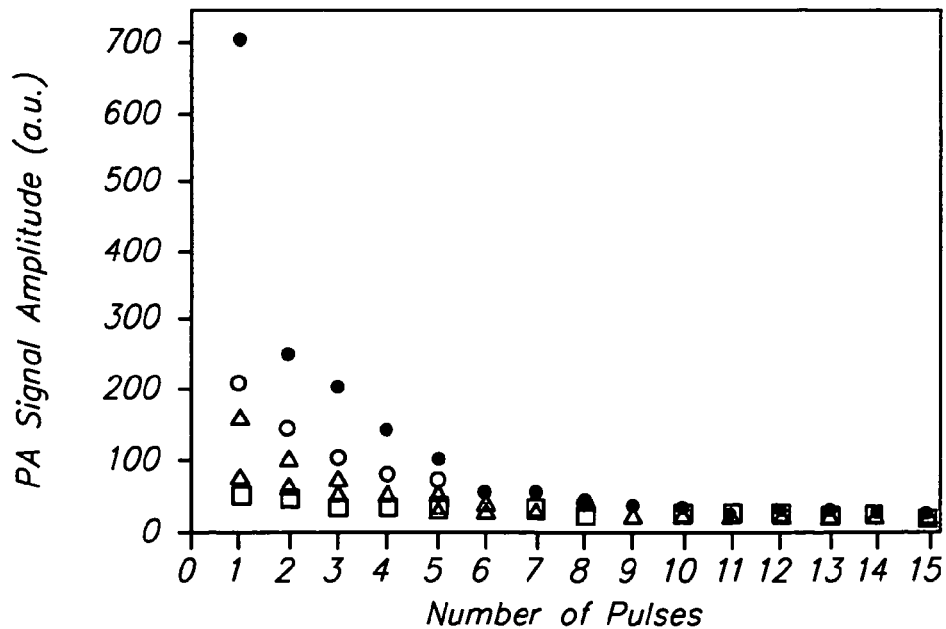

Our results indicate the high potential of CNTs as non-invasive NIR-responsive photothermal agents for therapeutic and nanotherapeutic applications. For example, selective killing of bacteria may be demonstrated using a combination of pulsed laser energy and NIR-responsive CNT NPs conjugated to the surface of *Escherichia coli* (FIG. 9). The results demonstrate irreparable damage to disease-causing pathogens and the usefulness of carbon nanotubes for non-invasive, in vivo photothermal antimicrobial nanotherapy. Obtained with PT microscope in PT imaging (PTI) mode, PT images demonstrated very high PT contrasts (as distribution of local PT image amplitude) of individual GNTs even at relatively low laser fluences in the range of 1-10 mJ/cm$^2$ at 850 nm (FIG. 10a). The PTI contrast and image size increased with increasing pulse energy (FIG. 10b), accompanied by bubble formation around overheated GNTs with the appearance of several overlapping microbubbles from closely located GNTs (FIG. 10e). The results are in line with our previous data with Au NPs. In thermolens mode, the integrated PT signals (FIGS. 10d-f) and PA signals (FIGS. 10g-i) demonstrated similar behaviors. In particular, the PA signal amplitudes gradually increased almost linearly with the increase in laser fluence of 1-10 mJ/cm$^2$, followed by further shifting to non-linear PA amplitude enhancements at the range of 0.5-10 J/cm$^2$ with the sign of slight saturation at higher energy above 10 J/cm$^2$ (FIG. 10j). Laser pulse number did not affect PA signal amplitudes at very low fluence, i.e., below 10 mJ/cm$^2$ (FIG. 10k). However, at higher fluences, significant decreases in PA signal amplitudes were observed with increase in pulse number. Especially, at 7.3 J/cm$^2$, the PA signal decreased ~3 times after the first laser pulse and disappeared after 10 pulses. This indicates the extremely high GNTs' NIR absorption capacity with very effective conversion of the absorbed energy to thermal energy, leading to GNTs' damage. The bubble lifetime and size, depending on the laser energy (4-100 mJ/cm$^2$), were ranged from 10 ns to 4 μs and from 200 nm to 20 respectively, implying the possibility of the well-controlled and highly localized cell damage (with minimal damage on surrounding normal cells) through proper selection of laser energy that generates bubbles with sizes comparable with the target area.

The efficiency of GNTs as PT sensitizers in pulse mode was compared with other promising NP-based PA/PT contrast agents, such as spherical Au NPs, GNRs, GNSs, and CNTs. Comparisons were made on the basis of bubble-formation thresholds, which are useful criteria to estimate the efficiency of laser energy conversion into heat and accompanied phenomena. The thresholds at the laser wavelength of 850 nm (8-ns pulse width) in water were found to be (1) 3.8±1.2 mJ/cm$^2$ for small clusters (3-5 NPs) of 11×100-nm GNTs, (2) 4 mJ/cm$^2$ for individual 155-nm GNSs, (3) 50-100 mJ/cm$^2$ for small clusters of 15×52-nm GNRs, (4) 80-300 mJ/cm$^2$ for clustered 40-nm spherical Au NPs (at 532 nm), and (5) 300-500 mJ/cm$^2$ for clustered 1.7×186-nm SWNTs. Even considering the slight differences in sizes and the potential variations in NPs' spatial distribution and dispersity, we can assume that the efficiency of GNTs is significantly higher than that of CNTs, spherical Au NPs, and even GNRs, and comparable with that of GNSs. However, compared to GNSs, the GNT's smaller diameter, rod-like shape with hollow core, and less rigidity (close to CNT's mechanical properties) could provide better targeting to small cell-surface biomolecules (5-10 nm), better clustering capability, and possibility to carry therapeutic payloads. The GNT's bubble formation threshold of ~3.8 mJ/cm$^2$ is significantly lower than the established NIR laser safety standard levels (35-100 mJ/cm$^2$ at wavelength of 700-1,100 nm), thus enabling the low toxic GNTs very promising for translation to humans. The adding of ethanol (40%) to water with GNTs led to further decrease the threshold to 0.9 mJ/cm$^2$ due to facilitating the bubble formation phenomena. Using an established calculation algorithm, the absorption cross-section of GNTs with the dimension of 11 nm×60 nm was estimated as 7.6×10$^{-10}$ cm$^2$ at 900 nm, which is comparable with that of GNRs (although GNTs have smaller diameters than GNRs) and higher than that of GNCs (3.5×10$^{-10}$ cm$^2$) and GNSs (~10$^{-10}$ cm$^2$), and much higher than that of conventional dyes such as indocyanine green (10$^6$ cm$^2$). Such unexpectedly high absorption cross-section could be explained by the synergy of longitudinal (as in GNRs) and gold-shell (as in GNSs) plasmon resonances in the hybrid GNTs. Our results hints that GNTs not only are the most blackest nanomaterials considering their strongest absorption, but also can be called as "nano black holes" owing to their unprecedentedly high absorption cross-section significantly (more than one order of magnitude) exceeding their geometric cross-section, which allows photons traveling far outside GNTs can be "trapped" by them in analogy to space black holes. In addition, the required laser fluence is much less than the established laser safety standard levels (35-100 mJ/cm$^2$), enabling gCNTs very promising for translation to humans. Moreover, the chances of the gCNTs' structural alterations are very minimal at these low laser fluences as our data indicate.

Figure 11A:
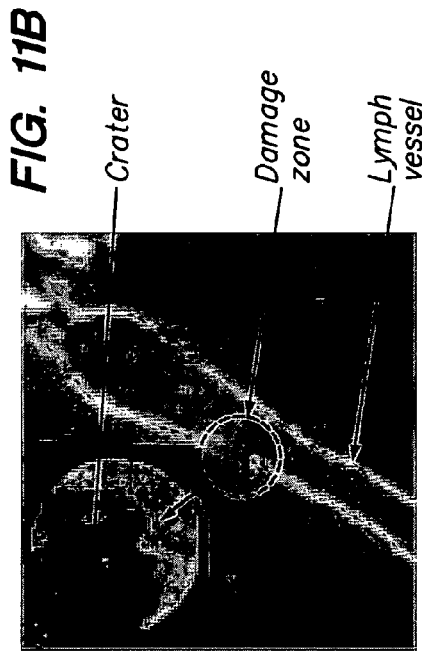
FIG. 11 illustrates in vivo molecular targeting of intact murine lymphatics with gCNT contrast agents guided by integrated PA/PT imaging for dynamic gCNT distribution in mesentery tissue and lymphatics. (a) Fragment of mouse mesentery with mapping area (square, 280 µm×280 field of interest). (b) Laser-induced localized (~10 µm in diameter) lymphatic wall damage around gCNTs targeted to LYVE-1. (c) Principle of selective targeting of endothelial LYVE-1 receptors with Ab-gCNT complex (left callout) and PA/PT detection schematics (right top and bottom, respectively). PT (d) and PA (h) background signals from selected mouse mesenteric area before gCNT administration. PT (e) and PA (i) signals at 60 min after administration of gCNTs with Abs. PT (f) and PA (j) signals from selected mouse mesenteric area at 15 min after administration of gCNTs with no Abs (control I). PT (g) and PA (k) signals from selected mouse mesenteric area at 60 min after administration of gCNTs with no Ab (control II). Each PT and PA image is presented in 3-D (bottom, brown background) and in 2-D (top, green background) simulations. White lines (solid and dash) indicate the lymphatic wall and valve. Total scanning time was 16 s. Laser parameters: wavelength 850 nm; pulse width 8 ns; fluence of 35 mJ/cm$^2$ (d, h), 10 mJ/cm$^2$ (e-g, i-k), 60 mJ/cm$^2$ (b).
Figure 11B:
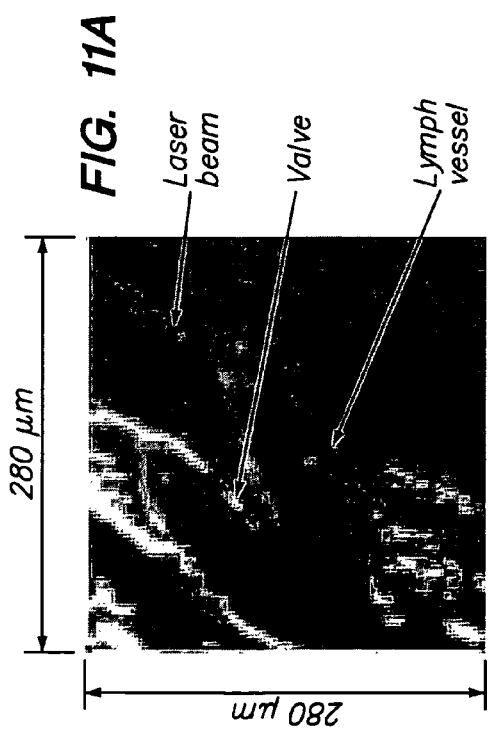
Figure 11C:
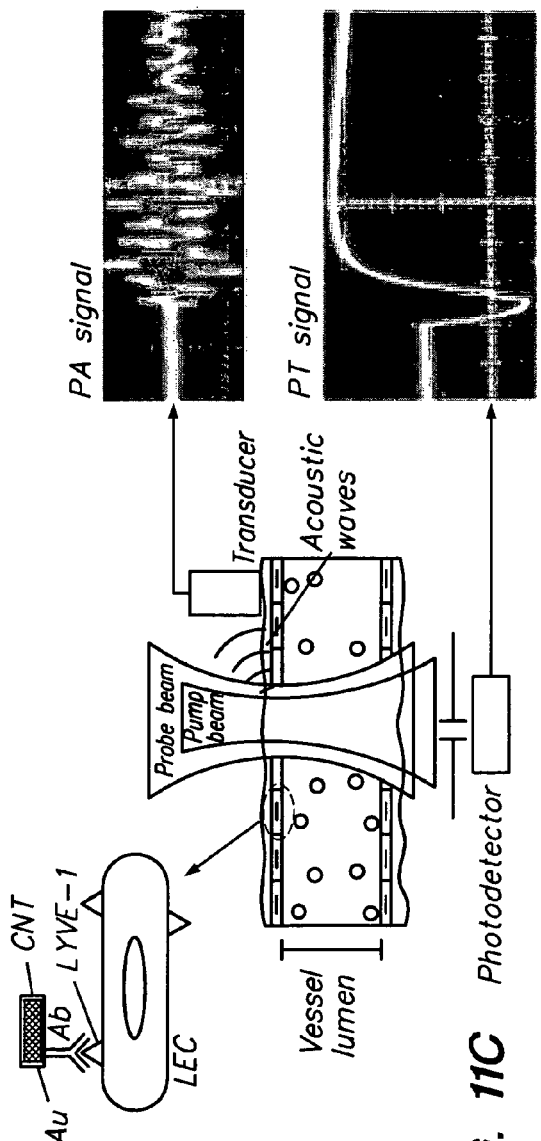

PA/PT imaging/mapping of nude mouse mesentery within the field of interest (FIG. 11a) was obtained by automatic scanning microscopic stage with mouse at fixed focused laser beam with diameter of 10 μm (FIG. 11c). The PT technique with the highest absorption sensitivity among currently available techniques revealed slight absorption heterogeneities of endogenous, low-absorbing mesenteric structures (FIG. 11d). PA technique provided lower absorption contrast background due to its low sensitivity to micro-scale local endogenous absorption (FIG. 11h). The administration of gCNTs conjugated with Abs, specific to the LYVE-1 receptors on the surface of nude mouse mesentery, led to the appearance of strong both PT and PA signals at the laser fluences of just 5-10 mJ/cm$^2$ (FIGS. 11e and 11i), which significantly (10-30 times) exceeded those from endogenous backgrounds (FIGS. 11d and 11h), and were preferentially located in lymphatic wall. Specifically, the mean signal amplitude from lymphatic wall was increased from 0.21±0.02 a.u. (background, before gCNT application) to 15.18±4.12 a.u. (at 60$^{th}$ min of gCNT action) (p=0.0006) for PA signals, and from 0.24±0.02 a.u. to 7.61±1.87 a.u. (p=0.0002) for PT signals. The signal amplitudes were stable during one-hour observation. The detected signals in vivo were well correlated in shape and amplitude with PA/PT signals obtained from the same GNTs in vitro. A few false-positive signals in the interstitium and fluctuating signals within lymphatics were observed, which might be associated with Ab-gCNTs up-taken by tissue macrophages and simultaneous washing-out, unbound Ab-gCNTs by lymph flow.

As a control, unconjugated gCNTs were also injected to mesentery surface. At the 15$^{th}$ min after gCNT administration, PA/PT mapping revealed randomly scattered low-level signals in the tissue interstitium and more profound signals in lymphatic flow above the background; however, no signals were observed in lymphatic wall (FIGS. 11f and 11j). Within next 60 min, signals became diminished in lymphatics due to their natural "washing" by lymph flow; however, a few signals with increased intensity were detected in interstitium (FIGS. 11g and 11k). The latter signals can be associated with the gCNTs up-taken and locally concentrated (or aggregated) in local tissue structures (e.g., by macrophages). These findings strongly suggest that the PA/PT signal distributions with Ab-gCNT conjugates (FIGS. 11e and 11i) are correlated with the position and local concentration of Ab-gCNTs bound to LYVE-1 receptors. Assessments of different lymph vessels showed highly heterogeneous gCNT spatial distributions along lymph vessels and gCNTs bound to the surface as clusters rather than single NPs in multiple discrete points. This data are in line with blood vessel wall targeting by QDs. The control study of gCNTs in vitro in suspension did not reveal gCNT aggregates. Thus, in analogy to blood vessels the observed phenomena may reflect the molecular diversity of the intact lymphatic vessel endothelia in vivo in terms of the differential expression of LYVE-1 receptors on LECs. We also observed strong signals from valve leaflets (FIGS. 11e, and 11i) that may indicate LYVE-1 expression by valvular endothelium, which has not been reported before.

About six-fold increase of laser energy (10 mJ/cm$^2$ to 60 mJ/cm$^2$) level led to non-linear, dramatic increase of PA/PT signals with dominant PA signals. This indicates the higher sensitivity of non-linear PA signals (compared to PT signals) to the local absorptions around nano-scale absorbing targets (i.e., gCNTs). These phenomena were accompanied by highly localized (within 5-10 μm), bubble-related damages of lymphatic walls around the zone of high local concentration of gCNTs or their clusters without notable changes in surrounding tissue (FIG. 4b). The integrated PA/PT technology with NM super contrast gCNTs may have broad-spectrum potential applications for non-invasive in vivo molecular imaging and highly precise and target-specific therapies. These would include treatment of lymphatic malformation, PA molecular detection of metastasis in lymph nodes and non-invasive PT node's purging, real-time tracking of gCNTs for blood/lymphangiography, selective gCNT-based drug delivery to lymphatics, and selective inhibition or stimulation of lymphangiogenesis to prevent metastasis progression or to restore lymphatic drainage at lymphedema, respectively.

Figure 12:
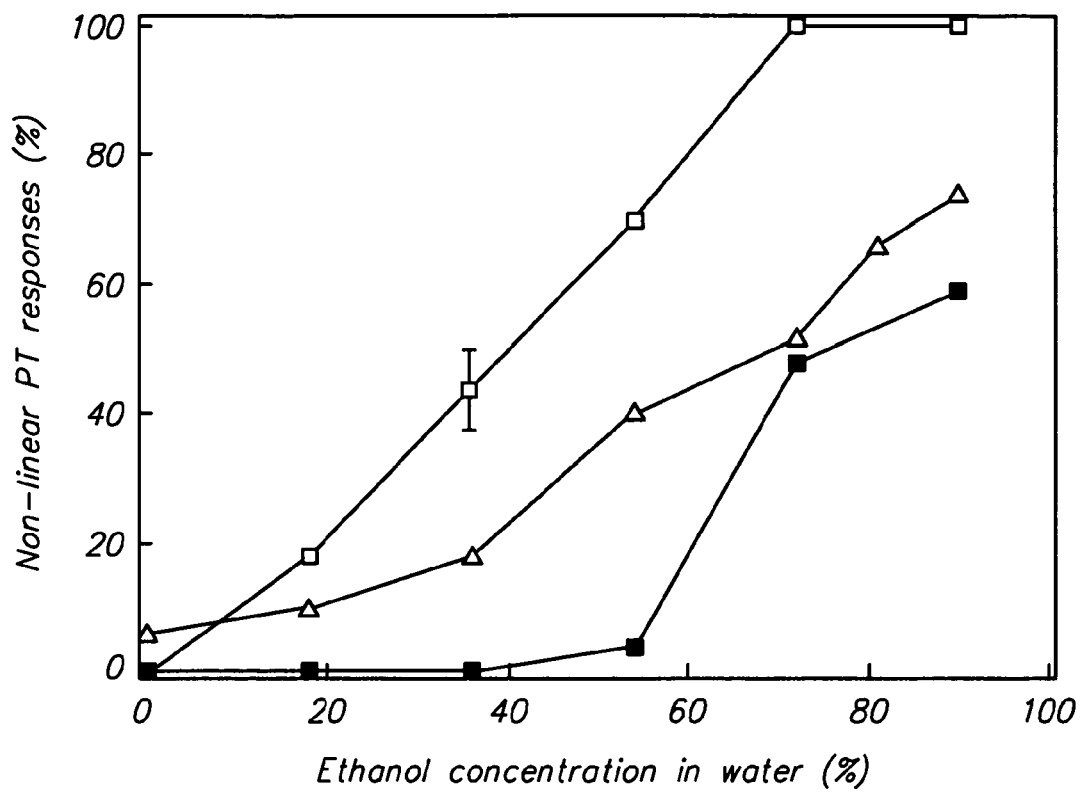
FIG. 12 Demonstrates the effect of ethanol concentrations on non-linear PT responses from thin suspension layer with clustered CNTs.

Ethanol in reaction mixtures significantly (up to two order) enhanced bubble formations (FIG. 12). The significant increase in the bubble formation for GNs and CNTs at the high ethanol concentration (90%) was associated not only with the thermal properties of ethanol but also with the ethanol-induced formation of large CNT clusters with the dimensions up to 10 μM×20 μm. The increased CNTs' hydrophobicity at the high ethanol concentration resulted in their increased adhesions. This strongly suggests that the delivery of ethanol to infected sites can significantly enhance the efficiency of selective nanophotothermolysis for their treatments. Ethanol (and likely solvents with similar properties) lead to more effective bubble formations and more profound heating in pulse mode because of its better thermodynamic parameters compared to water and its enhanced thermal expansion phenomena. As a result, the level of laser energy required to produce the bubbles around NPs and their nanoclusters is dramatically dropped, in particular for CNT clusters (more than two-order magnitude decrease). This approach to enhance PT antimicrobial nanotherapy is very promising because ethanol is already widely used for disinfection purposes. This approach can also be applied for PT cancer nanotherapy with both GNs or CNTs because particular percutaneous ethanol injection (PEI) is already used to treat different tumors, e.g., liver tumor. This technology can be further improved by the local and systemic ethanol administration in applications based on laser-induced bubble formation phenomena (e.g., cancer and vascular legion treatment). The gCNT acts similarly as CNT with the added advantage of biocompatibility, which CNT itself does not possess.

The gCNTs disclosed here are useful as a nanoparticle for an in vivo photothermal system and diagnostic contrast agent due to their optical properties, simple and robust conjugation techniques, and excellent biocompatibility. In addition, the substantial red shift in its surface plasmon resonance gives rise to a NIR absorption band. These optical properties in addition to biocompatibility make gCNTs useful for in vivo non-invasive photothermal therapy.

The degree of red plasmon resonance shifts as well as the absorption intensity may vary depending upon the size of CNT and thickness of the gold layer. Various sizes of CNTs, both well-dispersed SWNT and MWNT either of which may be in the range of about 50 nm, about 60 nm, about 75 nm, about 100 nm, about 125 nm, about 140 nm, about 160 nm, about 180 nm, or about 200 nm may be prepared based on the disclosed method of gCNT production. Their sizes will be determined using atomic force microscopy (AFM) and transmission electron microscopy (TEM). For each set of CNT with a proper size, e.g., 50 nm, various thicknesses of gold layers may be coated by controlling the time of Au(III)Cl3 reduction as well as the initial Au(III)Cl3 concentration. These variations allow for variations in the thickness of gold layered upon the carbon nanostructures. The optical properties of the gold-carbon nanostructure vary according to the thickness of the gold layers.

Gold colloids are functionalized with thiol groups based on the Brust reaction to form a stable layer. The thiol groups are then replaced by other ligands, such as, for example, amine (—NH2) or carboxyl (—COOH) groups, through the Murray place displacement reaction. The resulting modified layer may be used to covalently cross-link with biological elements functionalized with appropriate chemical reactive groups. For example, to confirm the Brust reaction, the gold layer may be linked with 5'-thiolmodified oligonucleotides. The functionalization of an oligonucleotide may be assayed, for example, by epi-fluorescence microscopy simply by incorporating a fluorophore, such as Cy3.

Examples of biocomponents that may be used in the present invention are Abs and DNA. Abs may be functionalized, for example, with thiol groups. Thiol groups may be generated by treating the antibody with dithiothreitol (DTT) to reduce disulfide bonds of the antibody. There are also kits commercially available for the thiol functionalization of antibody. Designed oligonucleotides may be purchased from commercial vendors with appropriate 3' and/or 5' modifications, such as, for example, 5'-amine, 3'-amine, 5'-thiol, and 3'-thiol modifications. Considering in vivo presence of DNase that degrades DNA, the stability of DNA might become an issue for in vivo application of this technology. When encountered, the challenge can be overcome by using peptide nucleic acids (PNA) which are DNA mimics with pseudo-peptides. PNAs are not recognized by nucleases or proteases; thus, they are resistant to enzyme degradation which would happen in the course of the delivery through blood. In addition, they act the same as DNAs, forming stable duplexes.

Figure 13A:
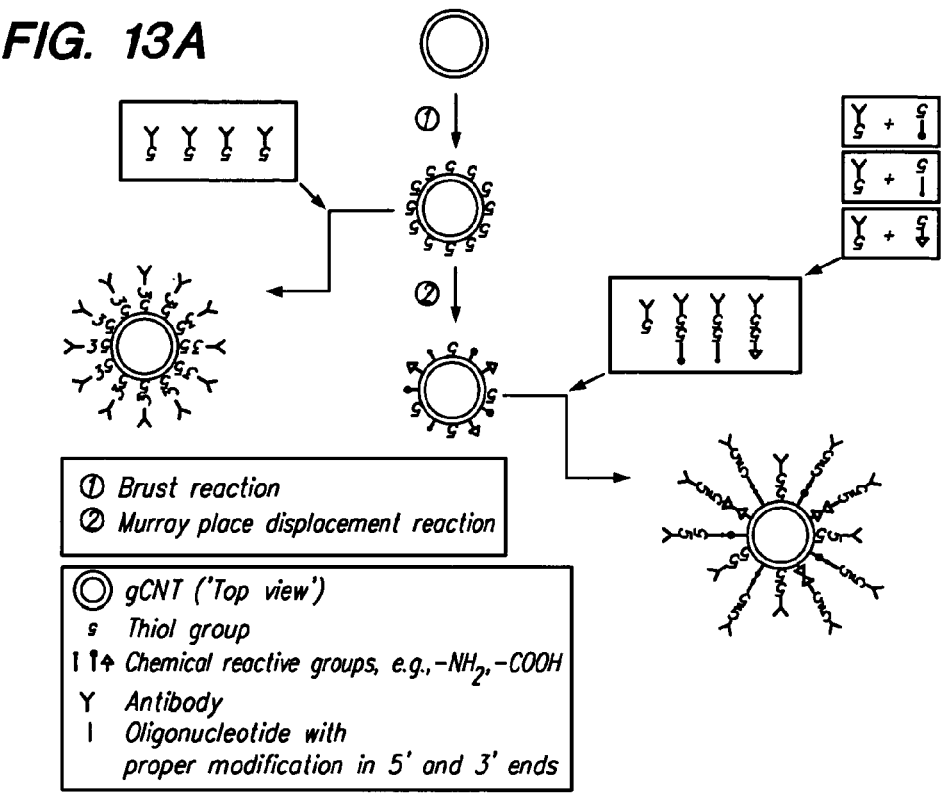
FIG. 13 illustrates a schematic of a multifunctional, multiplexing recognition unit assembly. (A) Chemical-reactive-group driven conjugations through (a) sulfhydryl linkage and (b) DNA/PNA as linkers after Murray place displacement reaction. (B) A short oligonucleotide as a 'molecular adaptor' to self-assemble DNA/PNA linked Abs. The adaptor comprises a series of shorter sequences complementary to the DNA/PNA attached to specific Abs, as well as a shorter sequence at one end that links the adaptor to the particle surface through (a) thiol linkage for NPs, such as gCNT and gold, and (b) DNA/PNA hybridization.
Figure 13B:
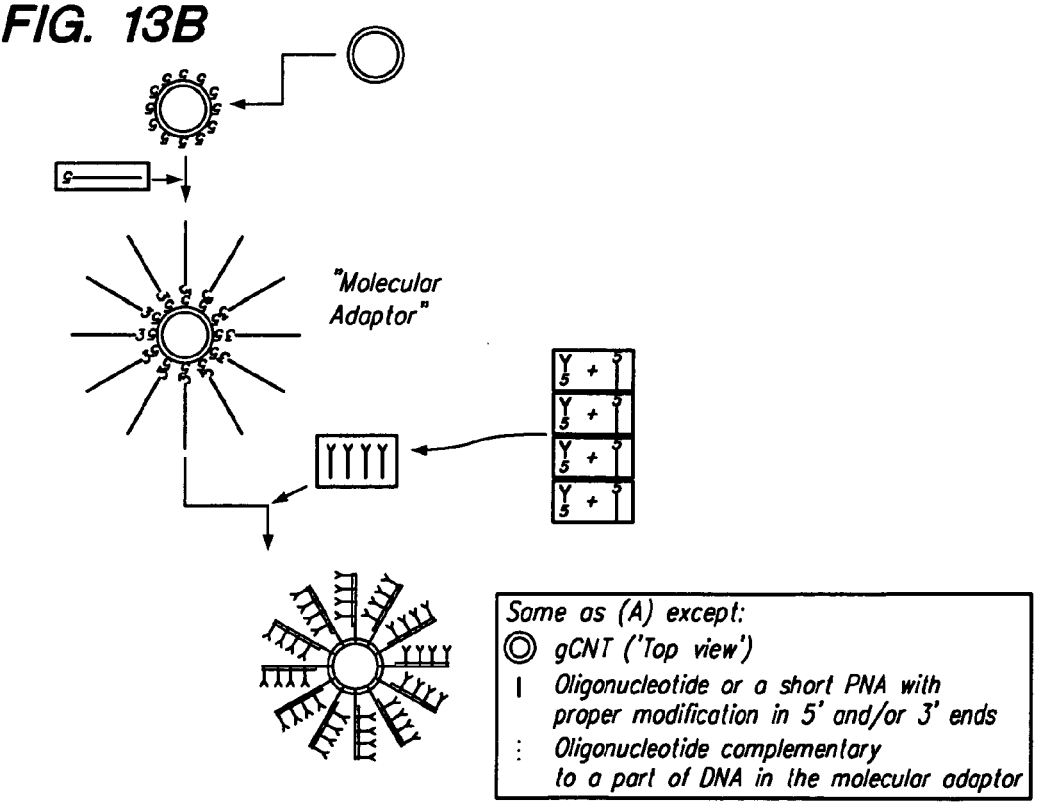

A finely controlled conjugation of different types of Abs (Ab) can be achieved by DNA owing to their selective molecular recognition properties. As depicted in FIG. 13, carefully designed DNA sequences may be cross-linked, or hybridized to the gCNT construct. The DNA sequence is designed to minimize mismatches and crosshybridizations, as well as to hybridize with multiple, shorter DNA for linking Ab in specific configurations. Each shorter DNA is functionalized to Abs, followed by self-assembly of the DNA through DNA-to-DNA hybridization between the gCNT attached DNA ('molecular adaptor') and DNA with Ab. This process is referred to as self-assembly because the final units form spontaneously without explicit positional control of component parts. This assembly occurs in parallel because the hybridization reactions between oligonucleotides for the recognition unit are not competitive. Moreover, control is achieved by assigning unique recognition elements or addresses, such as, for example, Ab, to specific DNA corresponding to specific locations in the DNA sequence of the molecular adaptor. The density of the molecular adaptor may be evaluated using fluorophore labeled complementary DNA of the molecular adaptor sequence. Fluorometeric and epi-fluorescence microscopic analyses may be performed to assess the density of molecular adaptor on the surface of the gCNT construct.

As noted above, the carefully designed DNA sequences may minimize undesirable mismatches and secondary structures. In addition, the size of the oligonucleotides may be varied such that they maintain stable duplexes at the physiological conditions. The stability of the DNA duplexes depends largely upon environmental temperature. Temperature dependence of DNA duplexes is characterized by melting temperature, Tm, which is defined as the temperature at which half of the double stranded DNA has dissociated into single stranded DNA. Tm varies depending upon the length of the DNA, its relative GC content, the salt concentration, and the nearest neighbor energetics. In other words, the properly designed DNA sequences should be stable under physiological conditions.

An alternative method is based on the Burst method followed by the Murray place displacement method. A gold colloid surface may be functionalized with thiol groups by the Burst method. These functionalized surfaces may be cross-linked with 5'-thiol modified short oligonucleotides. Due to the limitations on this method, the final product may have a different number of each antibody, if more than one antibody were attempted to be attached. It is also possible that some of the Abs may be missing. To avoid this, additional purification steps may be added after functionalizing the oligonucleotides to the gold and before attaching Abs. Sequential affinity chromatography with the counter-part reactive groups, such as, for example, —COOH for —NH2, allows for purification of the molecular adaptor with the optimal ligands attached. The effectiveness of the conjugations may be assessed by determining the density of Abs on the surface of the gCNT structures after (1) conjugations using DTT reduced rabbit IgG Abs linked with appropriately modified DNA, such as, for example, 5'-thiol modified and 3'-amine modified DNA to link carboxyl group on the surface and the reduced Abs and (2) fluorometeric analysis as well as epifluorescence microscopic analyses after addition of fluorophore, for example, Cy3, labeled goat anti-rabbit IgG.

A series of experiments with the bioconjugated gCNT systems may be performed with different cancer cells and Abs specific to the different cancerous cell types. The cancer cells for the experiments include the MDA-MB-231 and MFC-7 breast cancer cell line, and selected Abs specific to the cancer cells. Each cancerous cell line may be cultured in 12-well plates. Cultured cells may be incubated with gCNT structures in different media, including saline solution and whole human blood. After incubation (1-2 hr), the binding efficiency may be evaluated using silver enhancement stain (Amersham®) according to the manufacturer's protocol. Appropriate controls may be used, including no addition of gCNTs and addition of antibody-free gCNT assemblies. Selectivity of the conjugated antibody may be evaluated by incubating gCNT assemblies with one type of antibody in the wells containing other types of cells. Selectivity and efficiency of multi-antibody conjugates may be evaluated by carrying out the above experiments for multiple cell lines using the gCNTs conjugated with Abs to the selected cell lines.

In vitro photothermolysis may be performed using the optimized gCNT structures with various cancer cell lines used above. Cells may be cultured in 12 well plates in the ATCC prescribed medium. After incubation with antibody-conjugated gCNTs with the culture cells, NIR light of appropriate wavelengths may be administered to induce photothermal damage. After NIR exposure, cell viability, membrane damage, and gCNT binding may be evaluated using stains, such as, for example, calcein AM (Molecular Probe®) for cell viability, aldehyde-fixable fluorescein dextran dye (Molecular Probe®) for membrane damage, and silver enhancement stain for gCNT binding. The experiments may be done with appropriate controls, including no addition of gCNTs and addition of antibody-free gCNTs. Effectiveness of multi-antibody conjugates may be evaluated by carrying out the above experiment for multiple cell lines using the gCNTs conjugated with Abs to selected cell lines.

As various changes could be made in the above methods and compositions without departing from the scope of the invention, it is intended that all matter contained in the above description be interpreted as illustrative and not in a limiting sense. Unless explicitly stated to recite activities that have been done (i.e., using the past tense), illustrations and examples are not intended to be a representation that given embodiments of this invention have, or have not, been performed.

We claim:

1. A method of manufacture of a near-infrared responsive composition of matter effective in diagnosing and treating disease in a patient, the method comprising:
   (a) reacting a carbon nanotube solution and an effective concentration of gold to form a reaction mixture, wherein said reaction mixture comprises a ninety-five wet-percent aqueous solution and wherein said aqueous solution comprises a concentration of $HAuCl_4$; and
   (b) incubating said reaction mixture under conditions effective to form a near-infrared responsive composition of matter.

2. The method of claim 1 wherein said carbon nanotube is both the substrate and reducing agent.

3. The method of claim 1 wherein said reaction mixture further comprises a five wet-percent single-walled nanotube or multi-walled nanotube solution.

4. The method of claim 1 wherein a targeting moiety chosen from the group consisting of antibodies, deoxyribonucleic acids, peptide nucleic acids, folate, proteins, protein fragments, and small cell-surface biomolecules is coupled to said near-infrared responsive composition of matter.

* * * * *